United States Patent
Gobbi et al.

(10) Patent No.: US 10,457,684 B2
(45) Date of Patent: *Oct. 29, 2019

(54) [1,2,3]TRIAZOLO[4,5-D]PYRIMIDINE DERIVATIVES

(71) Applicant: Hoffmann-La Roche Inc., Little Falls, NJ (US)

(72) Inventors: Luca Gobbi, Buus (CH); Uwe Grether, Efringen-Kirchen (DE); Wolfgang Guba, Mullheim (DE); Julian Kretz, Berlin (DE); Rainer E. Martin, Basel (CH); Matthias Valentin Westphal, Zürich (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/228,535

(22) Filed: Dec. 20, 2018

(65) Prior Publication Data

US 2019/0127383 A1    May 2, 2019

Related U.S. Application Data

(63) Continuation of application No. PCT/EP2017/064988, filed on Jun. 20, 2017.

(30) Foreign Application Priority Data

Jun. 23, 2016 (EP) .................... 16175914

(51) Int. Cl.
C07D 487/04 (2006.01)
A61K 31/519 (2006.01)
C07D 519/00 (2006.01)

(52) U.S. Cl.
CPC .......... *C07D 487/04* (2013.01); *A61K 31/519* (2013.01); *C07D 519/00* (2013.01)

(58) Field of Classification Search
CPC ........................... C07D 487/04; A61K 31/519
USPC ....................... 544/254; 514/261.1
See application file for complete search history.

(56) References Cited

U.S. PATENT DOCUMENTS

| 7,776,889 | B2 | 8/2010 | Chackalamannil et al. |
| 8,741,906 | B2 | 6/2014 | Adam et al. |
| 9,056,866 | B2 | 6/2015 | Adam et al. |
| 9,067,943 | B2 | 6/2015 | Bissantz et al. |
| 9,505,762 | B2 | 11/2016 | Bendels et al. |
| 9,512,132 | B2 | 12/2016 | Grether et al. |
| 9,580,435 | B2 | 2/2017 | Grether et al. |
| 9,593,123 | B2 | 3/2017 | Grether et al. |
| 9,694,012 | B2 | 7/2017 | Grether et al. |
| 10,183,946 | B2 | 1/2019 | Grether et al. |
| 2019/0127384 | A1 | 5/2019 | Gobbi et al. |
| 2019/0127385 | A1 | 5/2019 | Gobbi et al. |
| 2019/0127386 | A1 | 5/2019 | Gobbi et al. |

FOREIGN PATENT DOCUMENTS

| FR | 2 887 550 A1 | 6/2005 |
| WO | 2011/045068 A2 | 4/2011 |
| WO | 2013/068306 A1 | 5/2013 |
| WO | 2013/076182 A1 | 5/2013 |
| WO | 2014/135507 A1 | 9/2014 |
| WO | 2014/177490 A1 | 11/2014 |
| WO | 2014/177527 A1 | 11/2014 |
| WO | 2015/032769 A1 | 3/2015 |
| WO | 2016/071375 A1 | 5/2016 |
| WO | 2017/220517 A1 | 12/2017 |
| WO | 2017/220544 A1 | 12/2017 |
| WO | 2018/015088 A1 | 1/2018 |

OTHER PUBLICATIONS

Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Layzer, Degenerative Diseases of the Nervous System, Cecil Textbook of Medicine, 20th Edition, vol. 2, pp. 2050-2057 (1996).*
Damasio, Alzheimer's Disease and Related Dementias, Cecil Textbook of Medicine, 20th Edition, vol. 2, pp. 1992-1996 (1996).*
Starowicz et al., Cannabinoid receptors and pain, WIREs Membr Transp Signal 2:121-132 (2013).*
Adeniyi et al., "New drug design with covalent modifiers" Expert Opinion on Drug Discovery 11(1):79-90 (2016).
Akhemetshina et al., "The cannabinoid receptor CB2 exerts antifibrotic effects in experimental dermal fibrosis" Arthritis Rheumatism 60(4):1129-1136 (2009).

(Continued)

*Primary Examiner* — Deepak R Rao
(74) *Attorney, Agent, or Firm* — Zong-Qiang Bill Tian

(57) ABSTRACT

The invention relates to a compound of formula (I)

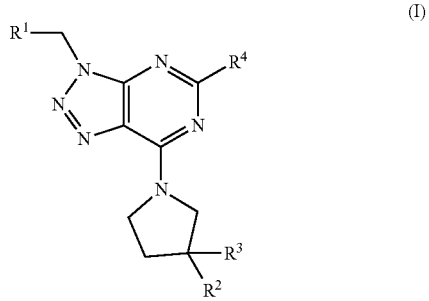

wherein $R^1$ to $R^4$ are defined as in the description and in the claims. The compound of formula (I) can be used as a medicament.

14 Claims, No Drawings

(56) References Cited

OTHER PUBLICATIONS

Ashton et al., "The cannabinoid CB2 receptor as a target for inflammation-dependent neurodegeneration" Current Neuropharmacology 5:73-80 (2007).

Bab et al., "Cannabinoid receptors and the regulation of bone mass" British Jounral of Pharmacology 153:182-188 (2008).

Batkai et al., "Cannabinoid-2 receptor mediates protection against hepatic ischemia/reperfusion injury" The FASEB Journal 21:1788-1800 (2007).

Beltramo et al., "Cannabinoid type 2 receptor as a target for chronic-pain" Mini-Reviews in Medicinal Chemistry 9:11-25 (2009).

Cabral et al., "Cannabinoid receptors in microglia of the central nervous system: immune functional relevance" Journal of Leukocyte Biology 78:1192-1197 (2005).

Cabral et al., "$CB_2$ receptors in the brain: role in central immune function" British Journal of Pharmacology 153:240-251 (2008).

Centonze et al., "The endocannabinoid system in peripheral lymphocytes as a mirror of neuroinflammatory diseases" Current Pharmaceutical Design 14:2370-2382 (2008).

Defer et al., "The cannabinoid receptor type 2 promotes cardiac myocyte and fibroblast survival and protects against ischemia/reperfusion-induced cardiomyopathy" The FASEB Journal 23:2120-2130 (2009).

Fakhfouri et al., "WIN55212-2 attenuates amyloid-beta-induced neuroinflammation in rats through activation of cannabinoid receptors and PPAR-g pathway" Neuropharmacology 63:653-666 (2012).

Feizi et al., "The preventive effect of cannabinoids on reperfusion-induced ischemia of mouse kidney" Experimental and Toxicologic Pathology 60:405-410 (2008).

Garcia-Gonzalez et al., "Cannabinoids inhibit fibrogenesis in diffuse systemic sclerosis fibroblasts" Rheumatology 48:1050-1056 (2009).

García-Gutierrez et al., "Chronic blockade of cannabinoid CB2 receptors induces anxiolytic-like actions associated with alterations in GABA receptors" British Jounral of Pharmacology 165:951-964 (2012).

International Preliminary Report on Patentability (IPRP) for PCT/EP2017/064988 dated Dec. 15, 2018.

International Search Report for PCT/EP2017/064988 dated Aug. 1, 2017.

Julien et al., "Antifibrogenic role of the cannabinoid receptor CB2 in the liver" Gastroenterology 128:742-755 (2005).

Lotersztajn et al., "CB2 receptors as new therapeutic targets for liver diseases" British Journal of Pharmacology 153:286-289 (2008).

Lotersztajn et al., "Le systeme cannabinoide: perspectives therapeutiques au cours des hepatopathies chroniques" Gastroenterol Clin Biol 31:255-258 (2007) (English abstract).

Lunn et al., "A Novel Cannabinoid Peripheral Cannabinoid Receptor-Selective Inverse Agonist Blocks Leukocyte Recruitment in Vivo" Journal of Pharmacology and Experimental Therapeutics 316(2):780-788 (2006).

Mach et al., "The role of the endocannabinoid system in atherosclerosis" Journal of Neuroendocrinology 20 (SUPPL 1):53-57 (2008).

Mallat et al., "Cannabinoid receptors as new targets of antifibrosing stategies during chronic liver diseases" Expert Opinion on Therapeutic Targets 11(3):403-409 (2007).

Miller et al., "$CB_2$ receptor-mediated migration of immune cells: it can go either way" British Journal of Pharmacology 153:299-308 (2008).

Munoz-Luque et al., "Regression of fibrosis after chronic stimulation of cannabinoid CB2 receptor in cirrhotic rats" Journal of Pharmacology and Experimental Therapeutics 324(2):475-483 (2008).

Nettekoven et al., "Novel Triazolopyrimidine-Derived Cannabinoid Receptor 2 Agonists as Potential Treatment for Inflammatory Kidney Diseases" ChemMedChem 11(2):179-189 (2016).

Pacher et al., "Endocannabinoids and cannabinoid receptors in ischaemia-reperfusion injury and preconditioning" British Journal of Pharmacology 153:252-262 (2008).

Pacher et al., "Is lipid signaling through cannabinoid 2 receptors part of a protective system?" Progress in Lipid Research 50:193-211 (2011).

Pasquini et al., "Design, Synthesis, and Pharmacological Characterization of Indol-3-ylacetamides, Indol-3-yloxoacetamides, and Indol-3-ylcarboxamides: Potent and Selective CB2 Cannabinoid Receptor Inverse Agonists" Journal of Medicinal Chemistry 55:5391-5402 (2012).

Preet et al., "Cannabinoid Receptors, CB1 and CB2, as Novel Targets for Inhibition of Non-Small Cell Lung Cancer Growth and Metastasis" Cancer Prevention Research 4:65-75 (2011).

Qiao et al., "Synthesis and biological evaluation of indole-2-carboxamides bearing photoactivatable functionalities as novel allosteric modulators for the cannabinoid CB1 receptor" European Journal of Medicinal Chemistry 121:517-529 (2016).

Sophocleous et al., "Cannabinoid receptor antagonists inhibit osteoclast formation in vitro and ovariectomy-induced bone loss in vivo through the CB1 and CB2 receptors" Calcified Tissue International Abstract OC18, 82:S31 (2008).

Ueda, "Involvement of cannabinoid CB2 receptors in the IgE-mediated triphasic cutaneous reaction in mice" Life Sciences 80:414-419 (2007).

Wright et al., "Cannabinoid $CB_2$ receptors in the gastrointestinal tract: a regulatory system in states of inflammation" British Jounral of Pharmacology 153:263-270 (2008).

Yang et al., "Inhibition of hepatic tumour necrosis factor-α attenuates the anandamide-induced vasoconstrictive response in cirrhotic rat livers" Liver International 29(5):678-685 (2009).

Zhang et al., "Cannabinoid $CB_2$ receptor activation decreases cerebral infarction in a mouse focal ischemia/reperfusion model" Journal of Cerebral Blood Flow & Metabolism 27:1387-1396 (2007).

\* cited by examiner

[1,2,3]TRIAZOLO[4,5-D]PYRIMIDINE DERIVATIVES

CROSS-REFERENCE TO RELATED APPLICATIONS

This application is a continuation of International Application No. PCT/EP2017/064988, filed on Jun. 20, 2017, which claims priority to European Patent Application No. 16175914.7, filed on Jun. 23, 2016, the contents of which are incorporated herein by reference in their entireties.

The present invention relates to novel [1,2,3]triazolo[4,5-d]pyrimidine derivatives with affinity for the type-2 cannabinoid (CB2) receptor, to the preparation thereof and to the diagnostic and therapeutic use thereof.

The invention relates in particular to a compound of formula (I)

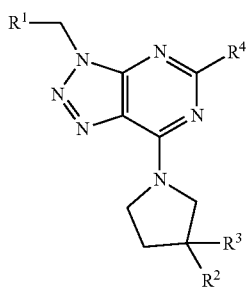

wherein
$R^1$ is a ring selected from phenyl, [1,2,5]oxadiazolyl, pyridinyl, pyrimidinyl and isoxazolyl, wherein said ring is substituted with one or two substituents independently selected from alkyl, haloalkyl, halogen, alkenyl, haloalkyldiazirenyl, alkynyldiazirenylalkylaminocarbonyl, alkynyldiazirenylalkylaminoalkyl, alkynyldiazirenylalkyloxyalkyl, alkynyldiazirenylalkylamino, alkynyldiazirenylalkyloxy and cyano;
$R^2$ and $R^3$ are independently selected from hydrogen, halogen and hydroxyl;
or $R^2$ and $R^3$ together with the carbon atom to which they are attached form diazirenyl;
provided that at least one of $R^1$ or $R^2$ and $R^3$ is a group comprising diazirenyl; and
$R^4$ is alkyl or phenylhaloalkyl;
or a pharmaceutically acceptable salt or ester thereof.

Novel [1,2,3]triazolo[4,5-d]pyrimidine derivatives that have high affinity and great selectivity towards the cannabinoid CB2 receptor have been found. These compounds have a modulatory effect on the activity of the CB2 receptor. The term 'modulatory effect' especially means agonist, antagonist and/or inverse agonist effects.

Agonists of the Cannabinoid Receptor 2 are useful for therapy and/or prophylaxis in a mammal. The compound of formula (I) is particularly useful in the treatment or prophylaxis of e.g. pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia/infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis.

Inverse agonists of the Cannabinoid Receptor 2 are useful for therapy and/or prophylaxis in a mammal.

The compound of formula (I) is particularly useful in the treatment or prophylaxis of pain, neuropathic pain, asthma, osteoporosis, inflammation, psychiatric diseases, psychosis, oncology, encephalitis, malaria, allergy, immunological disorders, arthritis, gastrointestinal disorders, psychiatric disorders rheumatoid arthritis, psychosis and allergy.

The cannabinoid receptors are a class of cell membrane receptors belonging to the G protein-coupled receptor superfamily. There are currently two known subtypes, termed Cannabinoid Receptor 1 (CB1) and Cannabinoid Receptor 2 (CB2). The CB1 receptor is mainly expressed in the central nervous (i.e. amygdala cerebellum, hippocampus) system and to a lesser amount in the periphery. CB2, which is encoded by the CNR2 gene, is mostly expressed peripherally, on cells of the immune system, such as macrophages and T-cells (Ashton, J. C. et al. Curr Neuropharmacol 2007, 5(2), 73-80; Miller, A. M. et al. Br J Pharmacol 2008, 153(2), 299-308; Centonze, D., et al. Curr Pharm Des 2008, 14(23), 2370-42), and in the gastrointestinal system (Wright, K. L. et al. Br J Pharmacol 2008, 153(2), 263-70). The CB2 receptor is also widely distributed in the brain where it is found primarily on microglia and not neurons (Cabral, G. A. et al. Br J Pharmacol 2008, 153(2): 240-51).

Modulators of the Cannabinoid Receptor 2 are useful for therapy and/or prophylaxis in a mammal.

The interest in CB2 receptor agonists has been steadily on the rise during the last decade (currently 30-40 patent applications/year) due to the fact that several of the early compounds have been shown to have beneficial effects in pre-clinical models for a number of human diseases including chronic pain (Beltramo, M. Mini Rev Med Chem 2009, 9(1), 11-25), atherosclerosis (Mach, F. et al. J Neuroendocrinol 2008, 20 Suppl 1, 53-7), regulation of bone mass (Bab, I. et al. Br J Pharmacol 2008, 153(2), 182-8), neuroinflammation (Cabral, G. A. et al. J Leukoc Biol 2005, 78(6), 1192-7), ischemia/reperfusion injury (Pacher, P. et al. Br J Pharmacol 2008, 153(2), 252-62), systemic fibrosis (Akhmetshina, A. et al. Arthritis Rheum 2009, 60(4), 1129-36; Garcia-Gonzalez, E. et al. Rheumatology (Oxford) 2009, 48(9), 1050-6), liver fibrosis (Julien, B. et al. Gastroenterology 2005, 128(3), 742-55; Munoz-Luque, J. et al. J Pharmacol Exp Ther 2008, 324(2), 475-83).

Ischemia/reperfusion (I/R) injury is the principal cause of tissue damage occurring in conditions such as stroke, myocardial infarction, cardiopulmonary bypass and other vascular surgeries, and organ transplantation, as well as a major mechanism of end-organ damage complicating the course of circulatory shock of various etiologies. All these conditions are characterized by a disruption of normal blood supply resulting in an insufficient tissue oxygenation. Re-oxygenation e.g., reperfusion is the ultimate treatment to restore normal tissue oxygenation. However the absence of oxygen and nutrients from blood creates a condition in which the restoration of circulation results in further tissue damage. The damage of reperfusion injury is due in part to the inflammatory response of damaged tissues. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane.

Remote ischemic preconditioning (RIPC) represents a strategy for harnessing the body's endogenous protective capabilities against the injury incurred by ischemia and reperfusion. It describes the intriguing phenomenon in which transient non-lethal ischemia and reperfusion of one organ or tissue confers resistance to a subsequent episode of "lethal" ischemia reperfusion injury in a remote organ or tissue. The actual mechanism through which transient ischemia and reperfusion of an organ or tissue confers protection is currently unknown although several hypotheses have been proposed.

The humoral hypothesis proposes that the endogenous substance (such as adenosine, bradykinin, opioids, CGRP, endocannabinoids, Angiotensin I or some other as yet unidentified humoral factor) generated in the remote organ or tissue enters the blood stream and activates its respective receptor in the target tissue and thereby recruiting the various intracellular pathways of cardioprotection implicated in ischemicpreconditioning.

Recent data indicates that endocannabinnoids and their receptors, in particular CB2 might be involved in preconditioning and contribute to prevent reperfusion injury by downregulation of the inflammatory response (Pacher, P. et al. Br J Pharmacol 2008, 153(2), 252-62). Specifically, recent studies using CB2 tool agonists demonstrated the efficacy of this concept for reducing the I/R injury in the heart (Defer, N. et al. Faseb J 2009, 23(7), 2120-30), the brain (Zhang, M. et al. J Cereb Blood Flow Metab 2007, 27(7), 1387-96), the liver (Batkai, S. et al. Faseb J 2007, 21(8), 1788-800) and the kidney (Feizi, A. et al. Exp Toxicol Pathol 2008, 60(4-5), 405-10).

Moreover, over the last few years, a growing body of literature indicates that CB2 can also be of interest in sub-chronic and chronic setting. Specific upregulation of CB1 and CB2 has been shown to be associated in animal models of chronic diseases associated with fibrosis (Garcia-Gonzalez, E. et al. Rheumatology (Oxford) 2009, 48(9), 1050-6; Yang, Y. Y. et al. Liver Int 2009, 29(5), 678-85) with a relevant expression of CB2 in myofibroblasts, the cells responsible for fibrosis progression.

Activation of CB2 receptor by selective CB2 agonist has in fact been shown to exert anti-fibrotic effect in diffuse systemic sclerosis (Garcia-Gonzalez, E. et al. Rheumatology (Oxford) 2009, 48(9), 1050-6) and CB2 receptor has emerged as a critical target in experimental dermal fibrosis (Akhmetshina, A. et al. Arthritis Rheum 2009, 60(4), 1129-36) and in in liver pathophysiology, including fibrogenesis associated with chronic liver diseases (Lotersztajn, S. et al. Gastroenterol Clin Biol 2007, 31(3), 255-8; Mallat, A. et al. Expert Opin Ther Targets 2007, 11(3), 403-9; Lotersztajn, S. et al. Br J Pharmacol 2008, 153(2), 286-9).

Inverse agonists of the Cannabinoid Receptor 2 are useful for therapy and/or prophylaxis in a mammal.

The compound of formula (I) is particularly useful in the treatment or prophylaxis of pain, neuropathic pain, asthma, osteoporosis, inflammation, psychiatric diseases, psychosis, oncology, encephalitis, malaria, allergy, immunological disorders, arthritis, gastrointestinal disorders, psychiatric disorders rheumatoid arthritis, psychosis and allergy.

The interest in CB2 receptor ligands has been steadily on the rise during the last decade (currently 30-40 patent applications/year). Evidence from different sources support the view that lipid endocannabinoid signaling through CB2 receptors represents an aspect of the mammalian protective armamentarium (Pacher, P. Prog Lipid Res 2011, 50, 193). Its modulation by either selective CB2 receptor agonists or inverse agonists/antagonists (depending on the disease and its stage) holds unique therapeutic potential in a huge number of diseases. For CB2 inverse agonists/antagonists therapeutic opportunities have been demonstrated for many pathological conditions including pain (Pasquini, S. J Med Chem 2012, 55(11): 5391), neuropathic pain (Garcia-Gutierrez, M. S. Br J Pharmacol 2012, 165(4): 951), psychiatric disorders (Garcia-Gutierrez, M. S. Br J Pharmacol 2012, 165(4): 951), psychosis (Garcia-Gutierrez, M. S. Br J Pharmacol 2012, 165(4): 951), osteoporosis and inflammation (Sophocleous, A. Calcif Tissue Int 2008, 82(Suppl. 1):Abst OC18), psychiatric diseases and psychosis (Garcia-Gutierrez, M. S. Br J Pharmacol 2012, 165(4): 951), oncology (Preet, A. Cancer Prev Res 2011, 4: 65), encephalitis and malaria (Zimmer, A. WO 2011045068), allergy and inflammation (Ueda, Y. Life Sci 2007, 80(5): 414), encephalitis and malaria (Zimmer, WO 2011045068), asthma (Lunn, C. A. J Pharmacol Exp Ther 2006, 316(2): 780), immunological disorders (Fakhfouri, G. Neuropharmacology 2012, 63(4): 653), rheumatoid arthritis (Chackalamannil, S. U.S. Pat. No. 7,776,889), arthritis (Lunn, C. A. J Pharmacol Exp Ther 2006, 316(2): 780), and gastrointestinal disorders (Barth, F. FR 2887550).

The compounds of the invention bind to and modulate the CB2 receptor and have lower CB1 receptor activity.

The compounds of the invention contain a diazirin moiety which can optionally be used to form a covalent bond with the CB2 receptor after photochemical activation. Such small organic molecules as covalent modifiers can be used for the detection and localisation of the target, for imaging, and for therapeutic use (compare e.g. Adebayo A Adeniyi, Ramesh Muthusamy & Mahmoud E S Soliman, Expert Opin. Drug Discov. (2016) 11(1):79-90).

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl. Particular examples of alkyl are methyl, ethyl and tert.-butyl.

The terms "halogen" or "halo", alone or in combination, signifies fluorine, chlorine, bromine or iodine and particularly fluorine, chlorine or bromine, more particularly fluorine and chlorine. The term "halo", in combination with another group, denotes the substitution of said group with at least one halogen, particularly substituted with one to five halogens, particularly one to four halogens, i.e. one, two, three or four halogens.

The term "haloalkyl", alone or in combination, denotes an alkyl group substituted with at least one halogen, particularly substituted with one to five halogens, particularly one to three halogens. Particular "haloalkyl" are trifluoromethyl and difluoromethyl.

The term "alkynyl", alone or in combination, signifies a straight-chain or branched hydrocarbon residue comprising a carbon-carbon triple bond and from 2 and up to 8, preferably up to 6, particularly preferred up to 4 carbon atoms. Examples of alkynyl are ethynyl and 1-butynyl.

The terms "hydroxyl" and "hydroxy", alone or in combination, signify the —OH group.

The term "oxy", alone or in combination, signifies the —O— group.

The term "alkoxy" or "alkyloxy", alone or in combination, signify a group of the formula alkyl-O— in which the term "alkyl" has the previously given significance, such as methoxy, ethoxy, n-propoxy, isopropoxy, n-butoxy, isobutoxy, sec.butoxy and tert.butoxy. A particular "alkoxy" is ethoxy.

The term "carbonyl", alone or in combination, signifies the —C(O)— group.

The term "amino", alone or in combination, signifies the primary amino group (—NH$_2$), the secondary amino group (—NH—), or the tertiary amino group (—N—).

The terms "diazirinyl" and "diazirenyl" are both used in the present description to designate the group

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3$^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The invention relates in particular to a compound of formula (I) wherein:
$R^1$ is a ring selected from phenyl, [1,2,5]oxadiazolyl, pyridinyl, pyrimidinyl and isoxazolyl, wherein said ring is substituted with one or two substituents independently selected from alkyl, haloalkyl, halogen, alkenyl, haloalkyldiazirenyl, alkynyldiazirenylalkylaminocarbonyl, alkynyldiazirenylalkylaminoalkyl, alkynyldiazirenylalkyloxyalkyl, alkynyldiazirenylalkylamino and alkynyldiazirenylalkyloxy;
$R^2$ and $R^3$ are independently selected from hydrogen, halogen and hydroxyl;
or $R^2$ and $R^3$ together with the carbon atom to which they are attached form diazirenyl;
provided that at least one of $R^1$ or $R^2$ and $R^3$ is a group comprising diazirenyl; and
$R^4$ is alkyl or phenylhaloalkyl;
or a pharmaceutically acceptable salt or ester thereof.

The invention further relates to:
A compound of formula (I) wherein $R^1$ is a ring selected from phenyl or [1,2,5]oxadiazolyl, wherein said ring is substituted with one substituent independently selected from alkyl, haloalkyl, haloalkyldiazirenyl, alkynyl and alkynyldiazirenylalkylaminocarbonyl;

A compound of formula (I) wherein $R^1$ is methyl[1,2,5]oxadiazolyl, trifluoromethylphenyl, trifluoromethyldiazirenylphenyl, ethynylphenyl or butynyldiazirenylethylaminocarbonyl[1,2,5]oxadiazolyl;

A compound of formula (I) wherein $R^2$ is hadrogen and $R^3$ is hydroxyl or $R^2$ and $R^3$ together with the carbon atom to which they are attached form diazirenyl;

A compound of formula (I) wherein $R^4$ is tert.-butyl or phenyldifluoromethyl;

A compound of formula (I) wherein $R^1$ is a ring selected from phenyl or [1,2,5]oxadiazolyl, wherein said ring is substituted with one or two substituents independently selected from alkyl, haloalkyl, haloalkyldiazirenyl, alkynyl, alkynyldiazirenylalkylaminocarbonyl and cyano;

A compound of formula (I) wherein $R^1$ is methyl[1,2,5]oxadiazolyl, trifluoromethylphenyl, trifluoromethyldiazirenylphenyl, ethynylphenyl, butynyldiazirenylethylaminocarbonyl[1,2,5]oxadiazolyl or (trifluoromethyldiazirenyl)(cyano)phenyl; and A compound of formula (I) wherein $R^2$ is hydrogen and $R^3$ is hydroxyl or $R^2$ and $R^3$ together with the carbon atom to which they are attached form diazirenyl or $R^2$ and $R^3$ are both fluorine at the same time.

The invention further relates to a compound of formula (I) selected from 5-tert-butyl-3-[(4-methyl-1,2,5-oxadiazol-3-yl)methyl]-7-(1,2,5-triazaspiro[2.4]hept-1-en-5-yl)-3H-[1,2,3]triazolo[4,5-d]pyrimidine;

5-[difluoro(phenyl)methyl]-7-(1,2,5-triazaspiro[2.4]hept-1-en-5-yl)-3-{[2-(trifluoromethyl)phenyl]methyl}-3H-[1,2,3]triazolo[4,5-d]pyrimidine;

5-tert-butyl-3-[(2-chlorophenyl)methyl]-7-(1,2,5-triazaspiro[2.4]hept-1-en-5-yl)-3H-[1,2,3]triazolo[4,5-d]pyrimidine;

5-tert-butyl-7-(3,3-difluoropyrrolidin-1-yl)-3-({2-[3-(trifluoromethyl)-3H-diaziren-3-yl]phenyl}methyl)-3H-[1,2,3]triazolo[4,5-d]pyrimidine;

5-tert-butyl-3-[(2-ethynylphenyl)methyl]-7-(1,2,5-triazaspiro[2.4]hept-1-en-5-yl)-3H-[1,2,3]triazolo[4,5-d]pyrimidine;

3-[(2-chlorophenyl)methyl]-5-[difluoro(phenyl)methyl]-7-(1,2,5-triazaspiro[2.4]hept-1-en-5-yl)-3H-[1,2,3]triazolo[4,5-d]pyrimidine;

5-[difluoro(phenyl)methyl]-3-[(4-methyl-1,2,5-oxadiazol-3-yl)methyl]-7-(1,2,5-triazaspiro[2.4]hept-1-en-5-yl)-3H-[1,2,3]triazolo[4,5-d]pyrimidine;

5-tert-butyl-3-({2-chloro-4-[3-(trifluoromethyl)-3H-diaziren-3-yl]phenyl}methyl)-7-(3,3-difluoropyrrolidin-1-yl)-3H-[1,2,3]triazolo[4,5-d]pyrimidine;

4-{[5-tert-butyl-7-(3,3-difluoropyrrolidin-1-yl)-3H-[1,2,3]triazolo[4,5-d]pyrimidin-3-yl]methyl}-N-{2-[3-(but-3-yn-1-yl)-3H-diaziren-3-yl]ethyl}-1,2,5-oxadiazole-3-carboxamide;

4-({5-tert-butyl-7-[(3S)-3-hydroxypyrrolidin-1-yl]-3H-[1,2,3]triazolo[4,5-d]pyrimidin-3-yl}methyl)-N-{2-[3-(but-3-yn-1-yl)-3H-diaziren-3-yl]ethyl}-1,2,5-oxadiazole-3-carboxamide;

N-{2-[3-(but-3-yn-1-yl)-3H-diaziren-3-yl]ethyl}-4-({5-[difluoro(phenyl)methyl]-7-(3,3-difluoropyrrolidin-1-yl)-3H-[1,2,3]triazolo[4,5-d]pyrimidin-3-yl}methyl)-1,2,5-oxadiazole-3-carboxamide;

5-tert-butyl-7-(3,3-difluoropyrrolidin-1-yl)-3-({3-[3-(trifluoromethyl)-3H-diaziren-3-yl]pyridin-2-yl}methyl)-3H-[1,2,3]triazolo[4,5-d]pyrimidine;

5-[difluoro(phenyl)methyl]-7-(3,3-difluoropyrrolidin-1-yl)-3-({3-[3-(trifluoromethyl)-3H-diaziren-3-yl]pyridin-2-yl}methyl)-3H-[1,2,3]triazolo[4,5-d]pyrimidine;

(3S)-1-[5-tert-butyl-3-({3-[3-(trifluoromethyl)-3H-diaziren-3-yl]pyridin-2-yl}methyl)-3H-[1,2,3]triazolo[4,5-d]pyrimidin-7-yl]pyrrolidin-3-ol;

(3S)-1-{5-[difluoro(phenyl)methyl]-3-({3-[3-(trifluoromethyl)-3H-diaziren-3-yl]pyridin-2-yl}methyl)-3H-[1,2,3]triazolo[4,5-d]pyrimidin-7-yl}pyrrolidin-3-ol;

5-tert-butyl-7-(3,3-difluoropyrrolidin-1-yl)-3-({4-[3-(trifluoromethyl)-3H-diaziren-3-yl]pyridin-3-yl}methyl)-3H-[1,2,3]triazolo[4,5-d]pyrimidine;

(3S)-1-[5-tert-butyl-3-({4-[3-(trifluoromethyl)-3H-diaziren-3-yl]pyridin-3-yl}methyl)-3H-[1,2,3]triazolo[4,5-d]pyrimidin-7-yl]pyrrolidin-3-ol;

5-[difluoro(phenyl)methyl]-7-(3,3-difluoropyrrolidin-1-yl)-3-({4-[3-(trifluoromethyl)-3H-diaziren-3-yl]pyridin-3-yl}methyl)-3H-[1,2,3]triazolo[4,5-d]pyrimidine;

(3S)-1-{5-[difluoro(phenyl)methyl]-3-({4-[3-(trifluoromethyl)-3H-diaziren-3-yl]pyridin-3-yl}methyl)-3H-[1,2,3]triazolo[4,5-d]pyrimidin-7-yl}pyrrolidin-3-ol;

5-tert-butyl-7-(3,3-difluoropyrrolidin-1-yl)-3-({5-[3-(trifluoromethyl)-3H-diaziren-3-yl]pyrimidin-4-yl}methyl)-3H-[1,2,3]triazolo[4,5-d]pyrimidine;

(3S)-1-[5-tert-butyl-3-({5-[3-(trifluoromethyl)-3H-diaziren-3-yl]pyrimidin-4-yl}methyl)-3H-[1,2,3]triazolo[4,5-d]pyrimidin-7-yl]pyrrolidin-3-ol;

5-[difluoro(phenyl)methyl]-7-(3,3-difluoropyrrolidin-1-yl)-3-({5-[3-(trifluoromethyl)-3H-diaziren-3-yl]pyrimidin-4-yl}methyl)-3H-[1,2,3]triazolo[4,5-d]pyrimidine;

(3S)-1-{5-[difluoro(phenyl)methyl]-3-({5-[3-(trifluoromethyl)-3H-diaziren-3-yl]pyrimidin-4-yl}methyl)-3H-[1,2,3]triazolo[4,5-d]pyrimidin-7-yl}pyrrolidin-3-ol;

5-tert-butyl-7-(3,3-difluoropyrrolidin-1-yl)-3-({3-[3-(trifluoromethyl)-3H-diaziren-3-yl]pyridin-4-yl}methyl)-3H-[1,2,3]triazolo[4,5-d]pyrimidine;

(3S)-1-[5-tert-butyl-3-({3-[3-(trifluoromethyl)-3H-diaziren-3-yl]pyridin-4-yl}methyl)-3H-[1,2,3]triazolo[4,5-d]pyrimidin-7-yl]pyrrolidin-3-ol;

5-[difluoro(phenyl)methyl]-7-(3,3-difluoropyrrolidin-1-yl)-3-({3-[3-(trifluoromethyl)-3H-diaziren-3-yl]pyridin-4-yl}methyl)-3H-[1,2,3]triazolo[4,5-d]pyrimidine;

(3S)-1-{5-[difluoro(phenyl)methyl]-3-({3-[3-(trifluoromethyl)-3H-diaziren-3-yl]pyridin-4-yl}methyl)-3H-[1,2,3]triazolo[4,5-d]pyrimidin-7-yl}pyrrolidin-3-ol;

5-tert-butyl-7-(3,3-difluoropyrrolidin-1-yl)-3-({5-[3-(trifluoromethyl)-3H-diaziren-3-yl]pyridin-2-yl}methyl)-3H-[1,2,3]triazolo[4,5-d]pyrimidine;

5-tert-butyl-7-(3,3-difluoropyrrolidin-1-yl)-3-({4-[3-(trifluoromethyl)-3H-diaziren-3-yl]pyridin-2-yl}methyl)-3H-[1,2,3]triazolo[4,5-d]pyrimidine;

5-tert-butyl-7-(3,3-difluoropyrrolidin-1-yl)-3-({5-[3-(trifluoromethyl)-3H-diaziren-3-yl]pyridin-3-yl}methyl)-3H-[1,2,3]triazolo[4,5-d]pyrimidine;

5-{[5-tert-butyl-7-(3,3-difluoropyrrolidin-1-yl)-3H-[1,2,3]triazolo[4,5-d]pyrimidin-3-yl]methyl}-N-{2-[3-(but-3-yn-1-yl)-3H-diaziren-3-yl]ethyl}-3-methyl-1,2-oxazole-4-carboxamide;

N-[(4-{[5-tert-butyl-7-(3,3-difluoropyrrolidin-1-yl)-3H-[1,2,3]triazolo[4,5-d]pyrimidin-3-yl]methyl}-1,2,5-oxadiazol-3-yl)methyl]-2-[3-(but-3-yn-1-yl)-3H-diaziren-3-yl]ethan-1-amine;

5-tert-butyl-3-{[4-({2-[3-(but-3-yn-1-yl)-3H-diaziren-3-yl]ethoxy}methyl)-1,2,5-oxadiazol-3-yl]methyl}-7-(3,3-difluoropyrrolidin-1-yl)-3H-[1,2,3]triazolo[4,5-d]pyrimidine;

2-[3-(but-3-yn-1-yl)-3H-diaziren-3-yl]-N-{[4-({5-[difluoro(phenyl)methyl]-7-(3,3-difluoropyrrolidin-1-yl)-3H-[1,2,3]triazolo[4,5-d]pyrimidin-3-yl}methyl)-1,2,5-oxadiazol-3-yl]methyl}ethan-1-amine;

3-{[4-({2-[3-(but-3-yn-1-yl)-3H-diaziren-3-yl]ethoxy}methyl)-1,2,5-oxadiazol-3-yl]methyl}-5-[difluoro(phenyl)methyl]-7-(3,3-difluoropyrrolidin-1-yl)-3H-[1,2,3]triazolo[4,5-d]pyrimidine;

5-tert-butyl-3-[(2-{2-[3-(but-3-yn-1-yl)-3H-diaziren-3-yl]ethoxy}phenyl)methyl]-7-(3,3-difluoropyrrolidin-1-yl)-3H-[1,2,3]triazolo[4,5-d]pyrimidine;

2-{[5-tert-butyl-7-(3,3-difluoropyrrolidin-1-yl)-3H-[1,2,3]triazolo[4,5-d]pyrimidin-3-yl]methyl}-N-{2-[3-(but-3-yn-1-yl)-3H-diaziren-3-yl]ethyl}aniline;

3-[(2-{2-[3-(but-3-yn-1-yl)-3H-diaziren-3-yl]ethoxy}phenyl)methyl]-5-[difluoro(phenyl)methyl]-7-(3,3-difluoropyrrolidin-1-yl)-3H-[1,2,3]triazolo[4,5-d]pyrimidine;

N-{2-[3-(but-3-yn-1-yl)-3H-diaziren-3-yl]ethyl}-2-({5-[difluoro(phenyl)methyl]-7-(3,3-difluoropyrrolidin-1-yl)-3H-[1,2,3]triazolo[4,5-d]pyrimidin-3-yl}methyl)aniline;

5-[difluoro(phenyl)methyl]-3-[(2-ethynylphenyl)methyl]-7-(1,2,6-triazaspiro[2.4]hept-1-en-6-yl)triazolo[4,5-d]pyrimidine;

5-[difluoro(phenyl)methyl]-7-(3,3-difluoropyrrolidin-1-yl)-3-[[2-ethynyl-6-[3-(trifluoromethyl)diazirin-3-yl]phenyl]methyl]triazolo[4,5-d]pyrimidine;

5-tert-butyl-7-(3,3-difluoropyrrolidin-1-yl)-3-[[2-ethynyl-6-[3-(trifluoromethyl)diazirin-3-yl]phenyl]methyl]triazolo[4,5-d]pyrimidine;
(3S)-1-[5-tert-butyl-3-[[2-ethynyl-6-[3-(trifluoromethyl)diazirin-3-yl]phenyl]methyl]triazolo[4,5-d]pyrimidin-7-yl]pyrrolidin-3-ol; and
(3S)-1-[5-[difluoro(phenyl)methyl]-3-[[2-ethynyl-6-[3-(trifluoromethyl)diazirin-3-yl]phenyl]methyl]triazolo[4,5-d]pyrimidin-7-yl]pyrrolidin-3-ol.

The invention further relates to a compound of formula (I) selected from
5-tert-butyl-3-[(4-methyl-1,2,5-oxadiazol-3-yl)methyl]-7-(1,2,5-triazaspiro[2.4]hept-1-en-5-yl)-3H-[1,2,3]triazolo[4,5-d]pyrimidine;
5-[difluoro(phenyl)methyl]-7-(1,2,5-triazaspiro[2.4]hept-1-en-5-yl)-3-{[2-(trifluoromethyl)phenyl]methyl}-3H-[1,2,3]triazolo[4,5-d]pyrimidine;
5-tert-butyl-7-(3,3-difluoropyrrolidin-1-yl)-3-({2-[3-(trifluoromethyl)-3H-diaziren-3-yl]phenyl}methyl)-3H-[1,2,3]triazolo[4,5-d]pyrimidine;
5-tert-butyl-3-[(2-ethynylphenyl)methyl]-7-(1,2,5-triazaspiro[2.4]hept-1-en-5-yl)-3H-[1,2,3]triazolo[4,5-d]pyrimidine;
4-({5-tert-butyl-7-[(3S)-3-hydroxypyrrolidin-1-yl]-3H-[1,2,3]triazolo[4,5-d]pyrimidin-3-yl}methyl)-N-{2-[3-(but-3-yn-1-yl)-3H-diaziren-3-yl]ethyl}-1,2,5-oxadiazole-3-carboxamide;
5-[difluoro(phenyl)methyl]-7-(3,3-difluoropyrrolidin-1-yl)-3-[[2-ethynyl-6-[3-(trifluoromethyl)diazirin-3-yl]phenyl]methyl]triazolo[4,5-d]pyrimidine; and
(3S)-1-[5-tert-butyl-3-[[2-ethynyl-6-[3-(trifluoromethyl)diazirin-3-yl]phenyl]methyl]triazolo[4,5-d]pyrimidin-7-yl]pyrrolidin-3-ol.

The preparation of compounds of formula (I) of the present invention may be carried out in sequential or convergent synthetic routes. Syntheses of the compounds of the invention are shown in the following scheme. The skills required for carrying out the reactions and purifications of the resulting products are known to those skilled in the art. The substituents and indices used in the following description of the processes have the significance given herein before unless indicated to the contrary. In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations*, 2nd Edition, Richard C. Larock. John Wiley & Sons, New York, N.Y. 1999). We found it convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 hours to several days will usually suffice to yield the described intermediates and compounds. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

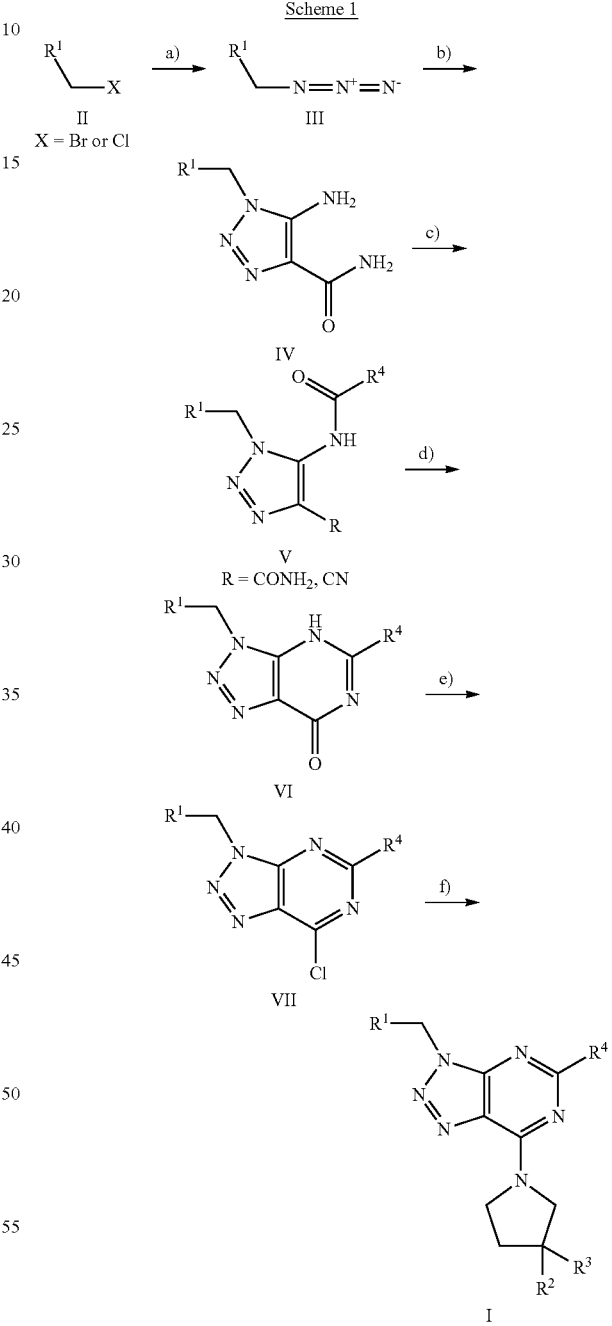

Scheme 1 a) Halides II are either commercially available or can be synthesized according to methods known in the art. These halides II are conveniently reacted with sodium azide in a suitable solvent such as acetonitrile, ethanol or DMF to afford azide derivatives III. Alternative preferred conditions involve the use of solvents like DMA, NMP or DMSO, even more preferred are NMP and DMSO. In polar aprotic solvents like NMP and DMSO, the alkylations can usually be conducted at lower temperature than for example in acetonitrile, often at room temperature to 40° C. (this is the case for example for BnCl, 1-chloro-2-(chloromethyl)benzene or PMB-Cl; this depends of course on the reactivity of the halides II) and hence provide a better process safety window (caution organic azides are of course known to be potentially dangerous and process safety has always to be carefully assessed). The addition of water can be beneficial as it increases the solubility of sodium azide and provided more robust kinetic profiles as it helps to dissolves hard clumps of NaN$_3$. It can also lead to a better filterability of the final azide reaction mixture. Filtration of the reaction mixture might be required for example when the following cycloaddition is performed in a continuous mode in small channels reactors. The azide is not isolated and its solution is best introduced in the next step. This also avoids its isolation which can also lead to safety issues.

b) Triazole derivatives IV can be prepared by a [3+2] cycloaddition of azide derivatives III with 2-cyanoacetamide in the presence of an appropriate base such as sodium methoxide or sodium ethoxide in a suitable solvent such as methanol, ethanol or DMF. Alternative preferred conditions involve reacting the azide with 2-cyanoacetamide in solvents like NMP or DMSO, in the presence of sodium hydroxide. The batch process is usually performed at room temperature to 50° C., preferably between room temperature and 40° C. (caution, process safety has always to be carefully assessed). The cycloaddition process is also amendable to continuous mode (for a relevant literature example, see *Org. Process Res. Dev.*, 2009, 13 (6), pp 1401-1406) and in this case the reaction temperature can be increased above 50° C., for example (but not limited to) between 50° C. and 90° C., preferably between 60° C. and 70° C.

c) Triazole derivatives V can be obtained by acylation of IV with an acyl-halide in the presence of a base such as DIEA, DMAP, pyridine and the like. Double acylation and the formation of nitrile side products have been observed. These can be significant when working for example in pyridine as solvent. However, these can be minimized when using DMA or NMP, preferably DMA as solvent instead of pyridine. Preferred conditions involves the use of 1.0-2 equiv. of pyridine and pivaloyl chloride, preferably 1.0 to 1.5 equiv., preferably around 1.5 equiv at 50-100° C., preferably between 75-85° C. These high boiling polar solvents also allow telescoping the following cyclization step which greatly simplifies the process.

d) Triazolopyrimidine derivatives VI can be prepared by intramolecular cyclization of triazole derivative V in the presence of a base such as KHCO$_3$, Na$_2$CO$_3$ and water either with or without a solvent such as methanol, ethanol, dioxane and toluene. Alternative preferred conditions involve the use of DMA or NMP as solvents, preferably DMA. The reaction can be performed in the presence of KHCO$_3$ at 130-170° C., preferably between 140 and 160° C. Compound VI may exist as a tautomer or a mixture of tautomers, for example:

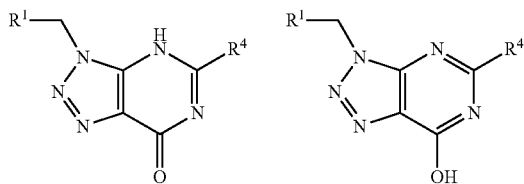

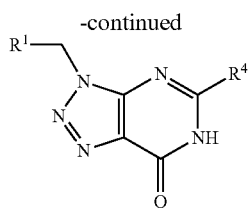

Optionally amido amides IV can be reacted with nitriles R$^4$—CN in the presence of a base such as K$_2$CO$_3$ in a solvent such as DMF, preferentially at temperatures close to the boiling point of the solvent to directly arrive at pyrimidones VI.

e) Chlorides VII can be obtained by reaction of VI with a chlorination reagent such as POCl$_3$, SOCl$_2$ or (COCl)$_2$ in the presence of an appropriate base such as N,N-diethyl aniline, lutidine, or pyridine. Alternative preferred conditions involve the use of the Vilsmeier reagent as chlorinating agent. It can also be generated in situ by reacting oxalyl chloride with DMF. The chlorination can be performed for example in acetonitrile, DCM or AcOEt, preferably in DCM. These conditions allow for mild reaction temperature and for example, avoid the quench of excess POCl$_3$ upon work-up. The crude product can be introduced in the next step.

f) Chlorides VII are conveniently reacted with amine nucleophiles in the presence of an appropriate base such as triethylamine, DIEA or DBU in a suitable solvent such as acetonitrile, methanol, toluene or DMF to yield triazolopyrimidine derivatives I.

These derivatives can be the final compounds, however preferably when R$^1$—CH$_2$=substituted benzyl group such as p-methoxy benzyl, these groups can be cleaved with TFA, CAN, hydrogenation and the like to access derivatives I (R$^1$—CH$_2$=H). R$^1$—CH$_2$=benzyl represents a suitable alternative protecting group. It avoids the use of PMB-Cl (for the preparation of the corresponding azide intermediate III) which is known to have some thermal stability issues (see for example *Organic Process Research* & Development 2005, 9, 1009-1012) and varying quality depending on the supplier. The benzyl group can be cleaved under standard hydrogenolysis conditions also for example in the presence of acids. When HCl is used, the derivatives I (R$^1$—CH$_2$=H) can potentially be isolated as salts.

The triazole derivatives I (R$^1$—CH$_2$=H) is conveniently reacted either with a halide (or sulfonate such as a mesylate, a nonaflate or a tosylate) in the presence of suitable base such as DIEA, DBU, K$_2$CO$_3$, or Cs$_2$CO$_3$ in a solvent such as DMF, dioxane or toluene, or alternatively with an alcohol under Mitsunobu reaction conditions using suitable diazodicarboxylate (DEAD, DIAD and the like) and phosphine such as PBu$_3$ or PPh$_3$ in an appropriate solvent such as THF, DCM, toluene to afford final triazolo-pyrimidine derivatives I.

If one of the starting materials, compounds of formulae II, acylation reagents used in step c) or amines used in step f), contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, 3$^{rd}$ edition) can be introduced before the critical step applying methods well known in the art. Such protecting groups can be removed at a later stage of the synthesis using standard methods known in the art.

If one or more compounds of formulae II to VII, acylation reagents used in step d) or amines used in step f), contain chiral centers, triazolopyrimidines of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

The invention also relates to a process for the preparation of a compound of formula (I) comprising the reaction of a compound of formula (A)

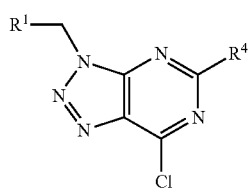

(A)

in the presence of a compound of formula (B)

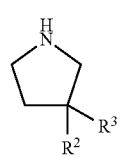

(B)

and a base, wherein $R^1$ to $R^4$ are as defined above.

In the process of the invention, the base is for example triethylamine, DIEA or DBU.

In the process of the invention, a solvent can be used, which can be selected for example from acetonitrile, methanol, toluene and DMF.

The invention thus also relates to a compound of formula (I) when manufactured according to a process of the invention.

Another embodiment of the invention provides a pharmaceutical composition or medicament containing a compound of the invention and a therapeutically inert carrier, diluent or excipient, as well as a method of using the compounds of the invention to prepare such composition and medicament. In one example, the compound of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compound of formula (I) is sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The invention thus also relates to:

A compound of formula (I) for use as therapeutically active substance;

A pharmaceutical composition comprising a compound of formula (I) and a therapeutically inert carrier;

The use of a compound of formula (I) for the preparation of medicaments for the treatment or prophylaxis of pain, neuropathic pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia/infarction, systemic sclerosis, thermal injury, burning, hypertrophic scars, keloids, gingivitis pyrexia, liver cirrhosis or tumors, regulation of bone mass, neurodegeneration, stroke, transient ischemic attack, uveitis, asthma, osteoporosis, psychiatric diseases, psychosis, oncology, encephalitis, malaria, allergy, immunological disorders, arthritis, gastrointestinal disorders, rheumatoid arthritis or allergy;

A compound of formula (I) for use in the treatment or prophylaxis of pain, neuropathic pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia/infarction, systemic sclerosis, thermal injury, burning, hypertrophic scars, keloids, gingivitis pyrexia, liver cirrhosis or tumors, regulation of bone mass, neurodegeneration, stroke, transient ischemic attack, uveitis, asthma, osteoporosis, psychiatric diseases, psychosis, oncology, encephalitis, malaria, allergy, immunological disorders, arthritis, gastrointestinal disorders, rheumatoid arthritis or allergy;

A method for the treatment or prophylaxis of pain, neuropathic pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia/infarction, systemic sclerosis, thermal injury, burning, hypertrophic scars, keloids, gingivitis pyrexia, liver cirrhosis or tumors, regulation of bone mass, neurodegeneration, stroke, transient ischemic attack, uveitis, asthma, osteoporosis, psychiatric diseases, psychosis, oncology, encephalitis, malaria, allergy, immunological disorders, arthritis, gastrointestinal disorders, rheumatoid arthritis or allergy, which method comprises administering an effective amount of a compound of formula (I) to a patient in need thereof; and The use of a compound of formula (I) for the detection or the imaging of the CB2 receptor.

The invention will now be illustrated by the following examples which have no limiting character.

EXAMPLES

Abbreviations
MS=mass spectrometry; CAN=ceric ammonium nitrate; CAN=chemical abstract service number; Ac=acetyl; DIEA=N,N-diisopropylethylamine; DBU=1,8-Diazabicyclo[5.4.0]undec-7-ene; DMF=dimethylformamide; HPLC=LC=high performance liquid chromatography; HRMS=high resolution mass spectrometry; MeCN=acetonitrile; NBS=N-Bromosuccinimide; NCS=N-Chloroosuccinimide; NMR data are reported in parts per million (δ) relative to internal tetramethylsilane and are referenced to the deuterium lock signal from the sample solvent ($d_6$-DMSO unless otherwise stated); coupling constants (J) are in Hertz; THF=tetrahydrofurane; TFA=trifluoroacetic acid; DCM=dichloromethane.

Example 1

5-tert-Butyl-3-[(4-methyl-1,2,5-oxadiazol-3-yl)methyl]-7-(1,2,5-triazaspiro[2.4]hept-1-en-5-yl)-3H-[1,2,3]triazolo[4,5-d]pyrimidine

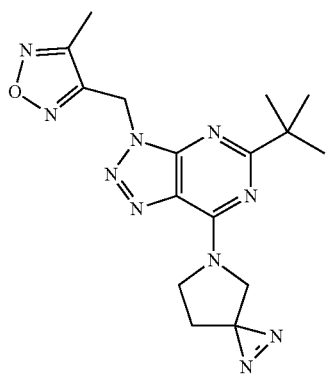 [SMILES: Cc1nonc1Cn1nnc2c(N3CCC4(C3)N=N4)nc(C(C)(C)C)nc21]

a) 3-((5-(tert-Butyl)-7-chloro-3H-[1,2,3]triazolo[4,5-d]pyrimidin-3-yl)methyl)-4-methyl-1,2,5-oxadiazole

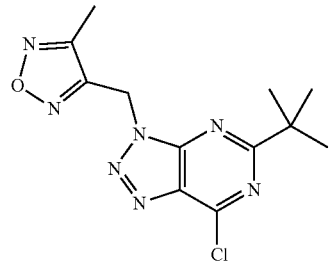 [SMILES: Cc1nonc1Cn1nnc2c(Cl)nc(C(C)(C)C)nc21]

5-(tert-Butyl)-3-((4-methyl-1,2,5-oxadiazol-3-yl)methyl)-3H-[1,2,3]triazolo[4,5-d]pyrimidin-7(4H)-one (CAS 1919022-49-3, 235 mg, 0.812 mmol, 1.00 equiv) and one drop of DMF were dissolved in $CH_2Cl_2$ (2.71 mL). Oxalyl chloride (80 μL, 0.89 mmol, 1.1 equiv) was added and the reaction mix was stirred overnight at room temperature. Celite was added and the solvent was removed. Flash chromatography on silica (0.5% MeOH in $CH_2Cl_2$) afforded 3-((5-(tert-butyl)-7-chloro-3H-[1,2,3]triazolo[4,5-d]pyrimidin-3-yl)methyl)-4-methyl-1,2,5-oxadiazole (230 mg, 0.757 mmol, 92% yield) as colorless solid. HRMS (MALDI+) 308.1021 (M+).

b) tert-Butyl 1,2,5-triazaspiro[2.4]hept-1-ene-5-carboxylate

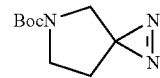

tert-Butyl 3-oxopyrrolidine-1-carboxylate (CAS 101385-93-7, 5.55 g, 30.0 mmol, 1.00 equiv) was dissolved in $Et_2O$ (5 mL) and cooled to −78° C. Ammonia (ca. 100 mL) was condensed into the flask and the reaction mixture was refluxed (dry ice condenser) for 6 h. Then the reaction mix was cooled back to −78° C. and a solution of hydroxylamine-O-sulfonic acid (3.73 g, 33.0 mmol, 1.10 equiv) in MeOH (20 mL) was added slowly. The dry-ice/acetone bath was removed and it was stirred for another 1.5 h at reflux (dry ice condenser). Then MeOH (45 mL) was added and the reaction mix was allowed to warm to room temperature overnight. The resulting suspension was filtered. The filter cake was washed with MeOH (2×30 mL). MeOH (50 mL) was added to the filtrate and it was concentrated to half of the original volume. MeOH (100 mL) was added and it was concentrated again to half of the original volume. $NEt_3$ (12 mL, 86 mmol, 2.87 equiv) was added and the reaction mixture was cooled to 0° C. The yellow solution was titrated with a solution of iodine in MeOH (ca. 7 g/100 mL) until an orange color remained. Celite was added and the solvent was removed. Flash chromatography on silica (10% EtOAc in hexanes) afforded tert-butyl 1,2,5-triazaspiro[2.4]hept-1-ene-5-carboxylate (876 mg, 4.44 mmol, 15% yield) as a yellow oil. $^1$H NMR (300 MHz, Chloroform-d) δ=3.63 (d, J=7.6, 2H), 3.00 (s, 2H), 1.69 (t, J=7.4, 2H), 1.46 (s, 9H).

c) 1,2,5-Triazaspiro[2.4]hept-1-ene hydrochloride

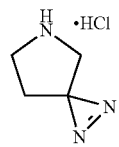

tert-Butyl 1,2,5-triazaspiro[2.4]hept-1-ene-5-carboxylate (272 mg, 1.38 mmol, 1 equiv) was dissolved in $Et_2O$ and HCl (4 M in dioxane, 3.45 mL, 13.8 mmol, 10 equiv) was added. When TLC indicated full consumption of starting material, the solvent was removed and the residue was washed with $Et_2O$ to give 1,2,5-triazaspiro[2.4]hept-1-ene hydrochloride (170 mg, 1.27 mmol, 92% yield) as a brown solid.

d) 5-tert-Butyl-3-[(4-methyl-1,2,5-oxadiazol-3-yl)methyl]-7-(1,2,5-triazaspiro[2.4]hept-1-en-5-yl)-3H-[1,2,3]triazolo[4,5-d]pyrimidine 3-((5-(tert-butyl)-7-chloro-3H-[1,2,3]triazolo[4,5-d]pyrimidin-3-yl)methyl)-4-methyl-1,2,5-oxadiazole (107 mg, 0.349 mmol, 1.00 equiv) was dissolved in $CH_2Cl_2$ (1.75 mL). 1,2,5-Triazaspiro[2.4]hept-1-ene hydrochloride (47 mg, 0.349 mmol, 1.00 equiv) and DIPEA (91 µL, 0.524 mmol, 1.5 equiv) were added and it was stirred for 30 min at room temperature. Celite was added and the solvent was removed. Flash chromatography on silica (1% EtOAc in $CH_2Cl_2$) afforded 5-tert-butyl-3-[(4-methyl-1,2,5-oxadiazol-3-yl)methyl]-7-(1,2,5-triazaspiro[2.4]hept-1-en-5-yl)-3H-[1,2,3]triazolo[4,5-d]pyrimidine (92 mg, 0.247 mmol, 71% yield) as colorless solid. HRMS (ESI+) 369.1896 (M+H$^+$).

Example 2

5-[Difluoro(phenyl)methyl]-7-(1,2,5-triazaspiro[2.4]hept-1-en-5-yl)-3-{[2-(trifluoromethyl)phenyl]methyl}-3H-[1,2,3]triazolo[4,5-d]pyrimidine

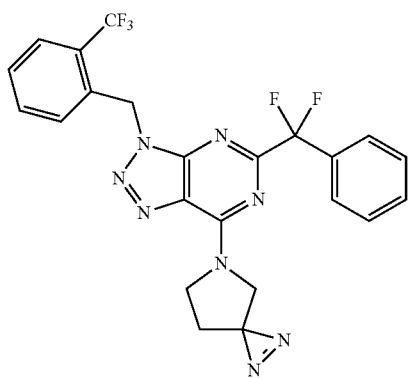 [SMILES: FC(F)(F)c1ccccc1Cn1nnc2c(N3CCC4(C3)N=N4)nc(C(F)(F)c3ccccc3)nc21]

a) 5-(Difluoro(phenyl)methyl)-3-(2-(trifluoromethyl)benzyl)-3H-[1,2,3]triazolo[4,5-d]pyrimidin-7(4H)-one

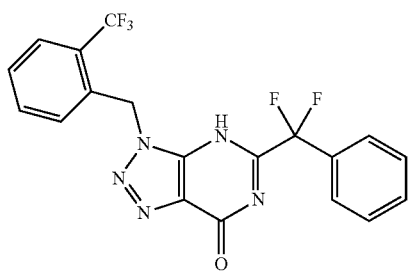 [SMILES: O=c1nc(C(F)(F)c2ccccc2)[nH]c2c1nnn2Cc1ccccc1C(F)(F)F]

5-Amino-1-(2-(trifluoromethyl)benzyl)-1H-1,2,3-triazole-4-carboxamide (CAS 93444-92-9, 201 mg, 0.710 mmol, 1.0 equiv) was added to a solution of 2,2-difluoro-2-phenylacetonitrile (162 mg, 1.06 mmol, 1.5 equiv) in DMF (2.3 mL) and $K_2CO_3$ (487 mg, 3.52 mmol, 5.0 equiv) was added. The flask was capped and heated to 90° C. overnight. EtOAc (100 mL) was added and the mix was washed with 5% aq. LiCl and brine. Drying over $MgSO_4$, filtration and concentration followed by flash chromatography on silica (60% EtOAc in hexanes) gave contaminated fractions. Fractions containing product were pooled and concentrated. Trituration of the residue with 2-PrOH and filtration afforded 5-(difluoro(phenyl)methyl)-3-(2-(trifluoromethyl)benzyl)-3H-[1,2,3]triazolo[4,5-d]pyrimidin-7(4H)-one (79 mg, 27% yield) as colorless solid. HRMS (ESI+) 422.1036 (M+H$^+$).

b) 7-Chloro-5-(difluoro(phenyl)methyl)-3-(2-(trifluoromethyl)benzyl)-3H-[1,2,3]triazolo[4,5-d]pyrimidine

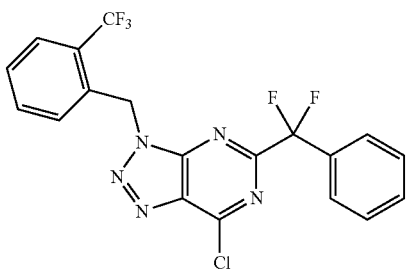 [SMILES: FC(F)(F)c1ccccc1Cn1nnc2c(Cl)nc(C(F)(F)c3ccccc3)nc21]

5-(Difluoro(phenyl)methyl)-3-(2-(trifluoromethyl)benzyl)-3H-[1,2,3]triazolo[4,5-d]pyrimidin-7(4H)-one (50 mg, 0.119 mmol, 1.0 eq) was dissolved in $CH_2Cl_2$ (1.2 mL) and DMF (3 drops) was added. The reaction mixture was cooled to 0° C. and oxalyl chloride (16 al, 0.178 mmol, 1.5 eq) was added dropwise. The cooling bath was removed and it was stirred at room temperature for 2 h. Additional oxalyl chloride (11.5 al, 0.118 mmol) was added and the reaction mixture was heated to reflux. After 1 h, the reaction mixture was poured into sat. $NaHCO_3$. Extraction with EtOAc, washing with 5% LiCl, brine, drying over $MgSO_4$ and concentration followed by flash chromatography on silica (10% EtOAc in hexanes) afforded 7-chloro-5-(difluoro(phenyl)methyl)-3-(2-(trifluoromethyl)benzyl)-3H-[1,2,3]triazolo[4,5-d]pyrimidine (43 mg, 82% yield) as a colorless oil. HRMS (ESI+) 440.0696 (M+H$^+$).

c) 5-[Difluoro(phenyl)methyl]-7-(1,2,5-triazaspiro[2.4]hept-1-en-5-yl)-3-{[2-(trifluoromethyl)phenyl]methyl}-3H-[1,2,3]triazolo[4,5-d]pyrimidine In analogy to the procedure described for the synthesis of 5-tert-butyl-3-[(4-methyl-1,2,5-oxadiazol-3-yl)methyl]-7-(1,2,5-triazaspiro[2.4]hept-1-en-5-yl)-3H-[1,2,3]triazolo[4,5-d]pyrimidine (example 1, step d) the title compound was prepared from 7-chloro-5-(difluoro(phenyl)methyl)-3-(2-(trifluoromethyl)benzyl)-3H-[1,2,3]triazolo[4,5-d]pyrimidine (21 mg, 0.048 mmol) and isolated as yellowish solid (18 mg, 75% yield). HRMS (ESI+) 501.1566 (M+H$^+$).

Example 3

5-tert-Butyl-3-[(2-chlorophenyl)methyl]-7-(1,2,5-triazaspiro[2.4]hept-1-en-5-yl)-3H-[1,2,3]triazolo[4,5-d]pyrimidine

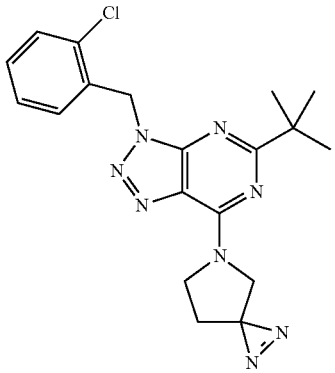 [SMILES: CC(C)(C)c1nc(N2CCC3(C2)N=N3)c2nnn(Cc3ccccc3Cl)c2n1]

In analogy to the procedure described for the synthesis of 5-tert-butyl-3-[(4-methyl-1,2,5-oxadiazol-3-yl)methyl]-7-(1,2,5-triazaspiro[2.4]hept-1-en-5-yl)-3H-[1,2,3]triazolo[4,5-d]pyrimidine (example 1, step d) the title compound was prepared from 5-(tert-butyl)-7-chloro-3-(2-chlorobenzyl)-3H-[1,2,3]triazolo[4,5-d]pyrimidine (CAS 1433362-85-6, 57 mg, 0.17 mmol, 1.0 equiv) and isolated as colorless oil (65 mg, 0.16 mmol, 96% yield). HRMS (ESI+) 397.1646 (M+H+).

Example 4

5-tert-Butyl-7-(3,3-difluoropyrrolidin-1-yl)-3-({2-[3-(trifluoromethyl)-3H-diaziren-3-yl]phenyl}methyl)-3H-[1,2,3]triazolo[4,5-d]pyrimidine

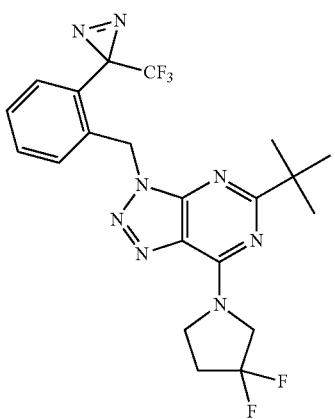 [SMILES: CC(C)(C)c1nc(N2CCC(F)(F)C2)c2nnn(Cc3ccccc3C3(C(F)(F)F)N=N3)c2n1]

a) 2,2,2-Trifluoro-1-(o-tolyl)ethanone O-tosyl oxime

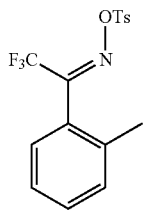

2,2,2-Trifluoro-1-(o-tolyl)ethanone oxime (CAS 387-57-5, 3.12 g, 15.3 mmol, 1.0 equiv) and DMAP (0.19 g, 1.53 mmol, 0.1 equiv) were dissolved in CH$_2$Cl$_2$ (51 mL) at room temperature. TsCl (3.51 g, 18.4 mmol, 1.2 equiv) was added over 10 min (exotherm) and it was stirred until TLC indicated full consumption of the starting material. Water (100 mL) was added and the mix was extracted with CH$_2$Cl$_2$ (3×50 mL). Drying over MgSO$_4$, filtration and concentration followed by flash chromatography on silica (30% CH$_2$Cl$_2$ in hexanes) afforded 2,2,2-trifluoro-1-(o-tolyl)ethanone O-tosyl oxime (5.24 g, 14.7 mmol, 96% yield) as a mixture of diastereomers. HRMS (ESI+) 358.0719 (M+H+).

b) 3-(o-Tolyl)-3-(trifluoromethyl)-3H-diazirine

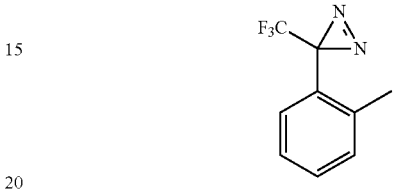

2,2,2-Trifluoro-1-(o-tolyl)ethanone O-tosyl oxime (2.89 g, 8.10 mmol, 1 equiv) was dissolved in Et$_2$O (22 mL), cooled to −78° C. and ammonia (ca. 40 mL) was introduced. The reaction mix was refluxed for 5 h (dry ice condenser) before being warmed to room temperature. Filtration (washing with Et$_2$O), concentration and flash chromatography on silica (10% Et$_2$O in pentane) afforded 3-(o-tolyl)-3-(trifluoromethyl)diaziridine (858 mg, 4.24 mmol, 53% yield), which was dissolved in Et$_2$O (17 mL) and treated with Ag$_2$O (1.15 g, 4.96 mmol, 1.17 equiv). Filtration over celite, concentration and flash chromatography on silica (100% pentane) afforded 3-(o-tolyl)-3-(trifluoromethyl)-3H-diazirine (786 mg, 3.93 mmol, 92% yield) as pale yellow oil. $^1$H NMR (300 MHz, Chloroform-d) δ=7.62-7.56 (m, 1H), 7.40-7.30 (m, 1H), 7.30-7.21 (m, 2H), 2.61 (s, 3H).

c) 3-(2-(Bromomethyl)phenyl)-3-(trifluoromethyl)-3H-diazirine

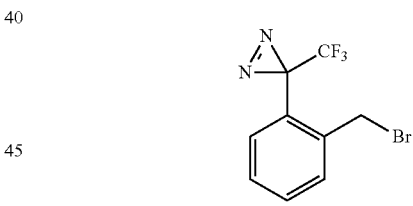

3-(o-Tolyl)-3-(trifluoromethyl)-3H-diazirine (0.5 g, 2.5 mmol, 1.0 equiv), NBS (1.1 g, 6.2 mmol, 2.5 equiv) and benzoyl peroxide (30 mg, 0.13 mmol, 0.05 equiv) were combined with CCl$_4$ (25 mL) and refluxed until TLC indicated full consumption of the starting material. Concentration followed by flash chromatography on silica afforded 3-(2-(bromomethyl)phenyl)-3-(trifluoromethyl)-3H-diazirine (445 mg, 1.48 mmol, 59% yield). $^1$H NMR (300 MHz, Chloroform-d) δ=7.71-7.64 (m, 1H), 7.55-7.34 (m, 3H), 4.79 (s, 2H).

d) 5-tert-Butyl-7-(3,3-difluoropyrrolidin-1-yl)-3-({2-[3-(trifluoromethyl)-3H-diaziren-3-yl]phenyl}methyl)-3H-[1,2,3]triazolo[4,5-d]pyrimidine 5-tert-Butyl-7-(3,3-difluoropyrrolidin-1-yl)-3H-[1,2,3]triazolo[4,5-d]pyrimidine (CAS 1438465-59-8, 42 mg, 0.15 mmol, 1.0 equiv) and 3-(2-(bromomethyl)phenyl)-3-(trifluoromethyl)-3H-diazirine (55 mg, 0.18 mmol, 1.2 equiv) were dissolved in DMF (0.7 mL) and DBU (29 μL, 0.19 mmol, 1.3 equiv) was added. The mixture was stirred for 1 h at room temperature. EtOAc (50 mL) was added and the mixture was washed with 5% aq. LiCl (10 mL) and brine (10 mL), dried over MgSO₄, filtered and concentrated. Flash chromatography on silica afforded 5-tert-butyl-7-(3,3-difluoropyrrolidin-1-yl)-3-({2-[3-(trifluoromethyl)-3H-diaziren-3-yl]phenyl}methyl)-3H-[1,2,3]triazolo[4,5-d]pyrimidine (24 mg, 0.05 mmol, 34% yield) as colorless oil. HRMS (ESI+) 481.1885 (M+H⁺).

Example 5

5-tert-Butyl-3-[(2-ethynylphenyl)methyl]-7-(1,2,5-triazaspiro[2.4]hept-1-en-5-yl)-3H-[1,2,3]triazolo[4,5-d]pyrimidine

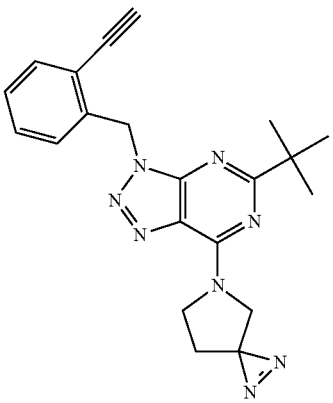 [SMILES: C#Cc1ccccc1Cn1nnc2c(N3CCC4(C3)N=N4)nc(C(C)(C)C)nc21]

a) 5-(tert-Butyl)-3-(2-((trimethylsilyl)ethynyl)benzyl)-3H-[1,2,3]triazolo[4,5-d]pyrimidin-7(4H)-one

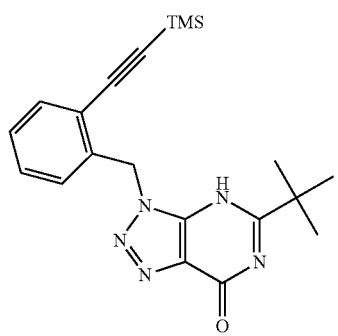 [SMILES: CC(C)(C)c1nc(=O)c2nnn(Cc3ccccc3C#C[Si](C)(C)C)c2[nH]1]

3-(2-Bromobenzyl)-5-(tert-butyl)-3H-[1,2,3]triazolo[4,5-d]pyrimidin-7(4H)-one (0.500 g, 1.38 mmol, 1.00 equiv, prepared in analogy to 3-(2-chlorobenzyl)-5-(tert-butyl)-3H-[1,2,3]triazolo[4,5-d]pyrimidin-7(4H)-one (CAS 1433362-83-4)), Pd(PhCN)₂Cl₂ (26 mg, 0.07 mmol, 0.05 equiv) and CuI (13 mg, 0.07 mmol) were added to a flame-dried flask and it was evacuated/backfilled with N₂ three times. Then dry toluene (7.7 mL) was added followed by PtBu₃ (1 M in toluene, 140 µL, 0.140 mmol, 0.1 equiv). After addition of diisopropylamine (0.295 mL, 2.07 mmol) and trimethylsilyl acetylene (290 µL, 2.07 mmol, 1.5 equiv) the flask was capped and heated to 50° C. overnight. The reaction was cooled to room temperature and filtered over celite (washing with CH₂Cl₂). The solvent was removed. The residue was purified by flash chromatography on silica (hexane/CH₂Cl₂/EtOAc 2:2:1) to afford 5-(tert-butyl)-3-(2-((trimethylsilyl)ethynyl)benzyl)-3H-[1,2,3]triazolo[4,5-d]pyrimidin-7(4H)-one (380 mg, 1.00 mmol, 73% yield) as foam. LRMS (ESI+) 380.9 (M+H⁺).

b) 5-(tert-Butyl)-3-(2-ethynylbenzyl)-3H-[1,2,3]triazolo[4,5-d]pyrimidin-7(4H)-one

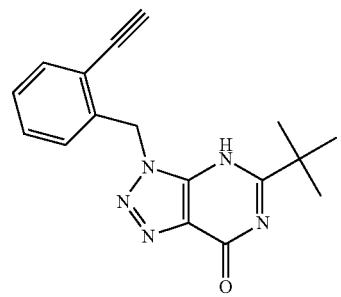 [SMILES: C#Cc1ccccc1Cn1nnc2c(=O)nc(C(C)(C)C)[nH]c21]

5-(tert-Butyl)-3-(2-((trimethylsilyl)ethynyl)benzyl)-3H-[1,2,3]triazolo[4,5dd]pyrimidin-7(4H)-one (165 mg, 0.435 mmol, 1.00 equiv) was dissolved in MeOH (2.17 mL). K₂CO₃ (300 mg, 2.17 mmol, 5.00 equiv) was added and it was stirred at room temperature until TLC indicated full consumption of starting material. After concentration, the residue was dissolved in CH₂Cl₂ (15 mL). The organic phase was washed with brine, dried over MgSO₄, filtered and concentrated. Flash chromatography on silica (30% EtOAc in CH₂Cl₂) afforded 5-(tert-butyl)-3-(2-ethynylbenzyl)-3H-[1,2,3]triazolo[4,5-d]pyrimidin-7(4H)-one (129 mg, 0.420 mmol, 97% yield) as colorless solid. LRMS (ESI+) 308.2 (M+H⁺).

c) 5-(tert-Butyl)-7-chloro-3-(2-ethynylbenzyl)-3H-[1,2,3]triazolo[4,5-d]pyrimidine

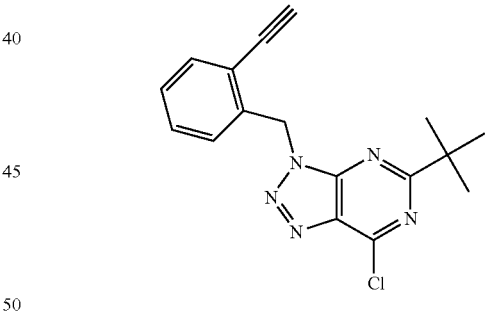

In analogy to the procedure described for the synthesis of 3-((5-(tert-butyl)-7-chloro-3H-[1,2,3]triazolo[4,5-d]pyrimidin-3-yl)methyl)-4-methyl-1,2,5-oxadiazole the title compound was prepared from 5-(tert-butyl)-3-(2-ethynylbenzyl)-3H-[1,2,3]triazolo[4,5-d]pyrimidin-7(4H)-one (100 mg, 0.325 mmol) and isolated as colorless solid (95 mg, 0.292 mmol, 90% yield). ¹H NMR (400 MHz, Chloroform-d) δ=7.57-7.52 (m, 1H), 7.38-7.27 (m, 3H), 6.06 (s, 2H), 3.38 (s, 1H), 1.44 (s, 9H).

d) 5-tert-Butyl-3-[(2-ethynylphenyl)methyl]-7-(1,2,5-triazaspiro[2.4]hept-1-en-5-yl)-3H-[1,2,3]triazolo[4,5-d]pyrimidine In analogy to the procedure described for the synthesis of 5-tert-butyl-3-[(4-methyl-1,2,5-oxadiazol-3-yl)methyl]-7-(1,2,5-triazaspiro[2.4]hept-1-en-5-yl)-3H-[1,2,3]triazolo[4, 5-d]pyrimidine (example 1, step d) the title compound was prepared from 5-(tert-butyl)-7-chloro-3-(2-ethynylbenzyl)-3H-[1,2,3]triazolo[4,5-d]pyrimidine (40 mg, 0.12 mmol), NEt₃ (34 µL, 0.25 mmol, 2.0 equiv) and the corresponding amine salt (1.2 equiv) and isolated as colorless oil (47 mg, 99% yield). HRMS (ESI+) 387.2036 (M+H$^+$).

Example 6

3-[(2-Chlorophenyl)methyl]-5-[difluoro(phenyl)methyl]-7-(1,2,5-triazaspiro[2.4]hept-1-en-5-yl)-3H-[1,2,3]triazolo[4,5-d]pyrimidine

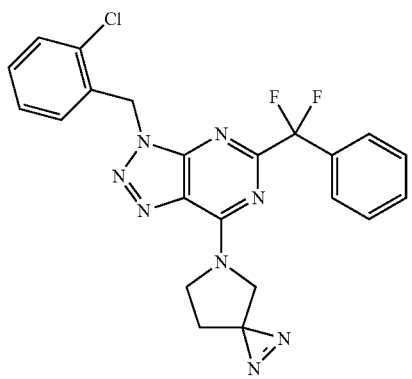

In analogy to the procedure described for the synthesis of 5-[difluoro(phenyl)methyl]-7-(1,2,5-triazaspiro[2.4]hept-1-en-5-yl)-3-{[2-(trifluoromethyl)phenyl]methyl}-3H-[1,2,3]triazolo[4,5-d]pyrimidine (example 2, steps a-c) the title compound was prepared from 5-amino-1-(2-chlorobenzyl)-1H-1,2,3-triazole-4-carboxamide (CAS 93444-91-8) and isolated as colorless oil. HRMS (ESI+) 467.1301 (M+H$^+$).

Example 7

5-[Difluoro(phenyl)methyl]-3-[(4-methyl-1,2,5-oxadiazol-3-yl)methyl]-7-(1,2,5-triazaspiro[2.4]hept-1-en-5-yl)-3H-[1,2,3]triazolo[4,5-d]pyrimidine

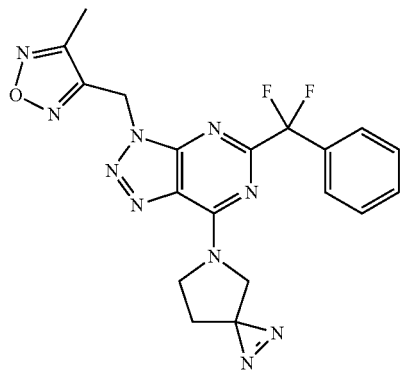 [SMILES: Cc1nonc1Cn1nnc2c(N3CCC4(C3)N=N4)nc(C(F)(F)c3ccccc3)nc21]

a) 5-Amino-1-((4-methyl-1,2,5-oxadiazol-3-yl)methyl)-1H-1,2,3-triazole-4-carboxamide

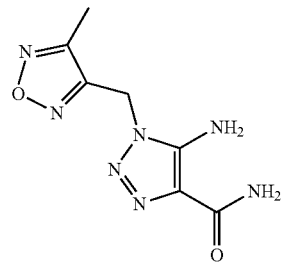 [SMILES: Cc1nonc1Cn1nnc(C(N)=O)c1N]

In analogy for the procedure described for the synthesis of 5-amino-1-(2-chlorobenzyl)-1H-1,2,3-triazole-4-carboxamide (CAS 93444-91-8) in US Patent 2013/116236 A1, the title compound was prepared from 4-methyl-3-chloromethyl-1,2,5-oxadiazole (CAS 62642-47-1, 2.5 g, 16.2 mmol), NaN₃ (1.1 g, 17.0 mmol) and 2-cyanoacetamide (2.04 g, 24.4 mmol) and isolated as beige solid (2.2 g, 9.9 mmol, 61% yield).

b) 5-(Difluoro(phenyl)methyl)-3-((4-methyl-1,2,5-oxadiazol-3-yl)methyl)-3H-[1,2,3]triazolo[4,5-d]pyrimidin-7(4H)-one

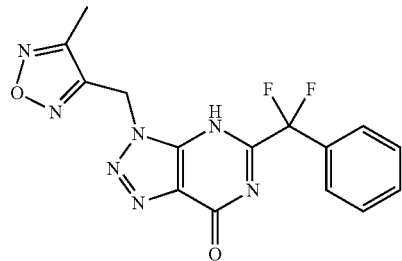 [SMILES: Cc1nonc1Cn1nnc2c(=O)nc(C(F)(F)c3ccccc3)[nH]c21]

5-Amino-1-((4-methyl-1,2,5-oxadiazol-3-yl)methyl)-1H-1,2,3-triazole-4-carboxamide (1.50 g, 6.72 mmol, 1.00 equiv), 2,2-difluoro-2-phenylacetonitrile (1.60 g, 10.5 mmol, 1.56 equiv) and K₂CO₃ (4.64 g, 33.6 mmol, 5.00 equiv) were combined with DMF (19.2 ml) and heated to 90° C. overnight. The reaction mix was cooled to room temperature and poured into icewater. Aq. HCl (1 M) was added until pH=3 and it was extracted with EtOAc (3×100 mL). The combined organics were washed with 5% aq. LiCl and brine, dried over MgSO₄, filtered and concentrated to leave a brown oil. Trituration of the residue with 2-PrOH and filtration afforded a pale yellow solid (1.45 g). The filtrate was concentrated and chromatographed on silica (CH₂Cl₂:acetone 9:1+1% MeOH). The fractions containing product were combined, concentrated and the residue again triturated with 2-PrOH to give another crop of 5-(difluoro(phenyl)methyl)-3-((4-methyl-1,2,5-oxadiazol-3-yl)methyl)-3H-[1,2,3]triazolo[4,5-d]pyrimidin-7(4H)-one (combined 1.72 g, 4.79 mmol, 71% yield). HRMS (ESI+) 360.1015 (M+H$^+$).

c) 3-((7-Chloro-5-(difluoro(phenyl)methyl)-3H-[1,2,3]triazolo[4,5-d]pyrimidin-3-yl)methyl)-4-methyl-1,2,5-oxadiazole

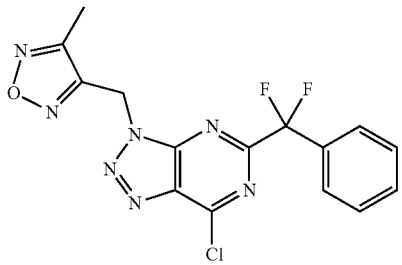 [SMILES: Cc1nonc1Cn1nnc2c(Cl)nc(C(F)(F)c3ccccc3)nc21]

5-(Difluoro(phenyl)methyl)-3-((4-methyl-1,2,5-oxadiazol-3-yl)methyl)-3H-[1,2,3]triazolo[4,5-d]pyrimidin-7(4H)-one (112 mg, 0.237 mmol, 1.00 equiv) was dissolved in CH$_2$Cl$_2$ (790 μL) and one drop of DMF was added. Oxalyl chloride (42 μL, 0.474 mmol, 2.00 equiv) was added dropwise and the mixture was heated to reflux for 1.5 h. The reaction mix was cooled to room temperature and diluted with EtOAc (30 mL). The organic phase was washed with water and brine, dried over MgSO$_4$, filtered and concentrated. Flash chromatography on silica (20% EtOAc in hexanes) afforded 3-((7-chloro-5-(difluoro(phenyl)methyl)-3H-[1,2,3]triazolo[4,5-d]pyrimidin-3-yl)methyl)-4-methyl-1,2,5-oxadiazole (80 mg, 0.21 mmol, 89% yield) as a colorless oil. HRMS (ESI+) 378.0677 (M+H$^+$).

d) 5-[Difluoro(phenyl)methyl]-3-[(4-methyl-1,2,5-oxadiazol-3-yl)methyl]-7-(1,2,5-triazaspiro[2.4]hept-1-en-5-yl)-3H-[1,2,3]triazolo[4,5-d]pyrimidine In analogy to the procedure described for the synthesis of 5-tert-butyl-3-[(4-methyl-1,2,5-oxadiazol-3-yl)methyl]-7-(1,2,5-triazaspiro[2.4]hept-1-en-5-yl)-3H-[1,2,3]triazolo[4,5-d]pyrimidine (example 1, step d) the title compound was prepared from 3-((7-chloro-5-(difluoro(phenyl)methyl)-3H-[1,2,3]triazolo[4,5-d]pyrimidin-3-yl)methyl)-4-methyl-1,2,5-oxadiazole (25 mg, 0.066 mmol) and isolated as colorless oil (25 mg, 0.057 mmol, 86% yield). HRMS (ESI+) 461.1365 (M+H$^+$).

Example 8

5-tert-Butyl-3-({2-chloro-4-[3-(trifluoromethyl)-3H-diaziren-3-yl]phenyl}methyl)-7-(3,3-difluoropyrrolidin-1-yl)-3H-[1,2,3]triazolo[4,5-d]pyrimidine

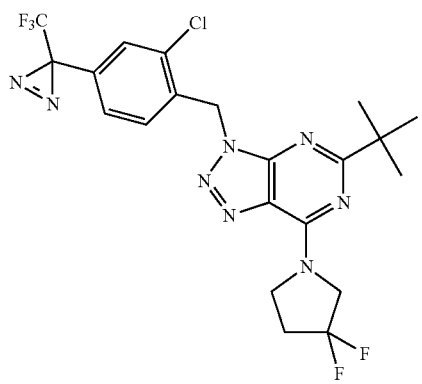 [SMILES: CC(C)(C)c1nc(N2CCC(F)(F)C2)c2nnn(Cc3ccc(C4(C(F)(F)F)N=N4)cc3Cl)c2n1]

a) 1-(3-Chloro-4-methylphenyl)-2,2,2-trifluoroethanone

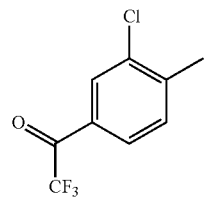

4-Bromo-2-chloro-1-methylbenzene (5.0 g, 24.3 mmol, 1.0 equiv) was dissolved in THF (50 mL) and cooled to −78° C. BuLi (1.6 M in hexanes, 17 mL, 27.2 mmol, 1.12 equiv) was added dropwise. After completion of the addition the reaction mixture was stirred for 30 min before 2,2,2-trifluoro-N-methoxy-N-methylacetamide (4.0 g, 25.5 mmol, 1.05 equiv) was added. The cooling bath was removed and it was stirred for 20 minutes. The reaction was quenched by the addition of sat. aq. NH$_4$Cl and extracted with EtOAc. The combined organics were washed with aq. HCl (1 M) and brine, dried over MgSO$_4$, filtered and concentrated. Flash chromatography on silica (20% Et$_2$O in pentane) afforded 1-(3-chloro-4-methylphenyl)-2,2,2-trifluoroethanone (5.17 g, 23.2 mmol, 95% yield) as yellow oil. $^1$H NMR (300 MHz, Chloroform-d) δ=8.04 (s, 1H), 7.89-7.83 (m, 1H), 7.45-7.39 (m, 1H), 2.49 (s, 3H).

b) 1-(3-Chloro-4-methylphenyl)-2,2,2-trifluoroethanone oxime

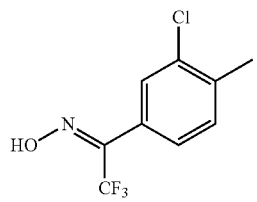

1-(3-Chloro-4-methylphenyl)-2,2,2-trifluoroethanone (3.67 g, 16.5 mmol, 1.0 equiv) and hydroxylamine hydrochloride (1.20 g, 17.3 mmol, 1.05 equiv) were combined with EtOH (32 mL). Pyridine (6.7 mL, 82 mmol, 5.0 equiv) was added and the mixture was stirred at 70° C. overnight. After cooling to room temperature, water (200 mL) was added and the mix was extracted with Et$_2$O. The combined organics were washed with HCl (aq. 0.5 M) and brine. The organic phase was dried over MgSO$_4$, filtered and concentrated. Flash chromatography on silica (10% EtOAc in hexanes) afforded 1-(3-chloro-4-methylphenyl)-2,2,2-trifluoroethanone oxime (3.45 g, 14.5 mmol, 88% yield). $^1$H NMR (400 MHz, Chloroform-d) δ=9.24 (s, 1H), 7.58 (s, 1H), 7.35 (app s, 2H), 2.44 (s, 3H).

c) 3-(4-(Bromomethyl)-3-chlorophenyl)-3-(trifluoromethyl)-3H-diazirine

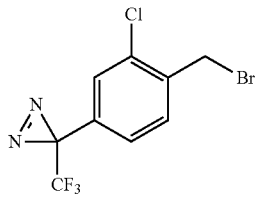 [SMILES: FC(F)(F)C1(c2ccc(CBr)c(Cl)c2)N=N1]

In analogy to the procedure described for the synthesis of 3-(2-(bromomethyl)phenyl)-3-(trifluoromethyl)-3H-diazirine (example 4, steps a-c) the title compound was prepared from 1-(3-chloro-4-methylphenyl)-2,2,2-trifluoroethanone oxime and isolated as yellow oil. $^1$H NMR (300 MHz, Chloroform-d) δ=7.48 (d, J=8.2, 1H), 7.23-7.18 (m, 1H), 7.09 (d, J=8.1, 1H), 4.56 (s, 2H).

d) 5-tert-Butyl-3-({2-chloro-4-[3-(trifluoromethyl)-3H-diaziren-3-yl]phenyl}methyl)-7-(3,3-difluoropyrrolidin-1-yl)-3H-[1,2,3]triazolo[4,5-d]pyrimidine In analogy to the procedure described for the synthesis of 5-tert-butyl-7-(3,3-difluoropyrrolidin-1-yl)-3-({2-[3-(trifluoromethyl)-3H-diaziren-3-yl]phenyl}methyl)-3H-[1,2,3]triazolo[4,5-d]pyrimidine (example 4, step d) the title compound was prepared from 5-tert-butyl-7-(3,3-difluoropyrrolidin-1-yl)-3H-[1,2,3]triazolo[4,5-d]pyrimidine (CAS 1438465-59-8, 54 mg, 0.19 mmol, 1.0 equiv) and 3-(4-(bromomethyl)-3-chlorophenyl)-3-(trifluoromethyl)-3H-diazirine (66 mg, 0.21 mmol, 1.1 equiv) and isolated as yellowish wax (45 mg, 0.09 mmol, 46% yield). HRMS (ESI+) 515.1494 (M+H$^+$).

Example 9

4-{[5-tert-Butyl-7-(3,3-difluoropyrrolidin-1-yl)-3H-[1,2,3]triazolo[4,5-d]pyrimidin-3-yl]methyl}-N-{2-[3-(but-3-yn-1-yl)-3H-diaziren-3-yl]ethyl}-1,2,5-oxadiazole-3-carboxamide

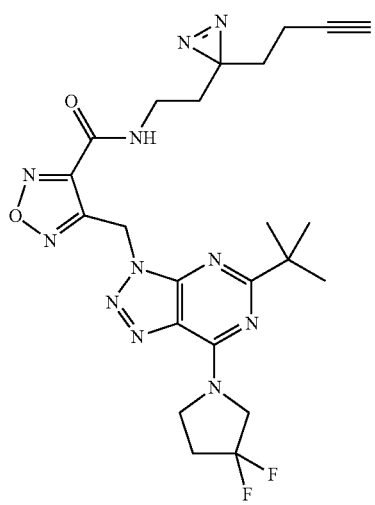 [SMILES: C#CCCC1(CCNC(=O)c2nonc2Cn2nnc3c(N4CCC(F)(F)C4)nc(C(C)(C)C)nc32)N=N1]

a) N-(2-(3-(But-3-yn-1-yl)-3H-diazirin-3-yl)ethyl)-4-(hydroxymethyl)-1,2,5-oxadiazole-3-carboxamide

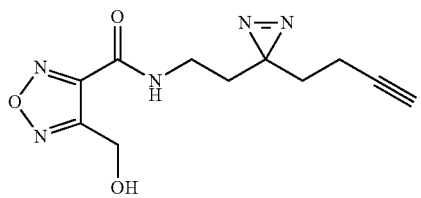 [SMILES: C#CCCC1(CCNC(=O)c2nonc2CO)N=N1]

3-(But-3-ynyl)-3-(2-aminoethyl)-3H-diazirine (CAS 1450752-97-2, 96 mg, 0.70 mmol, 1.0 equiv) was dissolved in toluene (2.3 mL) and cooled to 0° C. AlMe$_3$ (2 M in toluene, 370 µL, 0.74 mmol, 1.06 equiv) was added slowly. After 30 min at 0° C., a solution 6H-furo[3,4-c][1,2,5]oxadiazol-4-one (CAS 73314-58-6, 106 mg, 0.84 mmol, 1.2 equiv) in toluene (1 mL) was added slowly. The cooling bath was removed and the mixture was stirred at room temperature for 1 h. A precipitate formed, THF (1 mL) was added and stirring was continued for 1 h. The reaction was quenched by the addition of a sat. aq. solution of Rochelle's salt (2 mL) and water (2 mL). EtOAc (5 mL) was added and the reaction mix was vigorously stirred for 1 h. Extraction with EtOAc (3×5 mL), washing with brine, drying over MgSO$_4$, filtration and concentration followed by flash chromatography on silica (25% EtOAc in hexanes) afforded N-(2-(3-(but-3-yn-1-yl)-3H-diazirin-3-yl)ethyl)-4-(hydroxymethyl)-1,2,5-oxadiazole-3-carboxamide (171 mg, 0.65 mmol, 93% yield) as yellowish oil. HRMS (ESI+) 264.1096 (M+H$^+$).

b) (4-((2-(3-(But-3-yn-1-yl)-3H-diazirin-3-yl)ethyl)carbamoyl)-1,2,5-oxadiazol-3-yl)methyl methanesulfonate

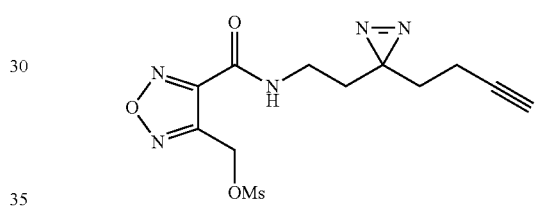

N-(2-(3-(but-3-yn-1-yl)-3H-diazirin-3-yl)ethyl)-4-(hydroxymethyl)-1,2,5-oxadiazole-3-carboxamide (87 mg, 0.33 mmol, 1.0 equiv) and NEt$_3$ (69 µL, 0.50 mmol, 1.5 equiv) were dissolved in CH$_2$Cl$_2$ (1.1 mL) and cooled to 0° C. MsCl (31 µL, 0.40 mmol, 1.2 equiv) was added. After 30 minutes, MeOH (0.1 mL) and celite were added and the solvent was removed. Flash chromatography on silica (30% EtOAc in hexanes to 40% EtOAc in hexanes) afforded (4-((2-(3-(but-3-yn-1-yl)-3H-diazirin-3-yl)ethyl)carbamoyl)-1,2,5-oxadiazol-3-yl)methyl methanesulfonate (90 mg, 0.26 mmol, 80% yield) as colorless oil. HRMS (ESI+) 364.0692 (M+H$^+$).

c) 4-{[5-tert-Butyl-7-(3,3-difluoropyrrolidin-1-yl)-3H-[1,2,3]triazolo[4,5-d]pyrimidin-3-yl]methyl}-N-{2-[3-(but-3-yn-1-yl)-3H-diaziren-3-yl]ethyl}-1,2,5-oxadiazole-3-carboxamide In analogy to the procedure described for the synthesis of 5-tert-butyl-7-(3,3-difluoropyrrolidin-1-yl)-3-({2-[3-(trifluoromethyl)-3H-diaziren-3-yl]phenyl}methyl)-3H-[1,2,3]triazolo[4,5-d]pyrimidine the title compound was prepared from (4-((2-(3-(but-3-yn-1-yl)-3H-diazirin-3-yl)ethyl)carbamoyl)-1,2,5-oxadiazol-3-yl)methyl methanesulfonate (45 mg, 0.13 mmol, 1.0 equiv), NEt$_3$ (37 µL, 0.26 mmol, 2.0 equiv) and 5-tert-butyl-7-(3,3-difluoropyrrolidin-1-yl)-3H-[1,2,3]triazolo[4,5-d]pyrimidine (CAS 1438465-59-8, 37 mg, 0.13 mmol, 1.0 equiv) and isolated as colorless oil (13 mg, 0.025 mmol, 19% yield). HRMS (ESI$^+$) 528.2387 (M+H$^+$).

Example 10

4-({5-tert-Butyl-7-[(3S)-3-hydroxypyrrolidin-1-yl]-3H-[1,2,3]triazolo[4,5-d]pyrimidin-3-yl}methyl)-N-{2-[3-(but-3-yn-1-yl)-3H-diaziren-3-yl]ethyl}-1,2,5-oxadiazole-3-carboxamide

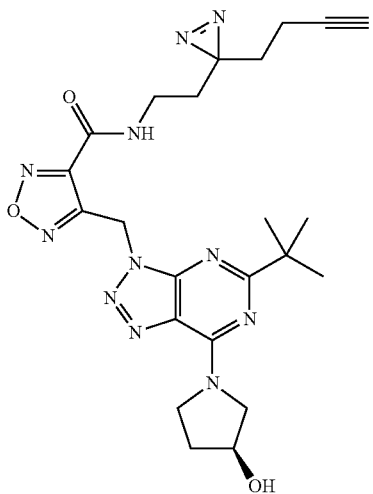 [SMILES: C#CCCC1(CCNC(=O)c2nonc2Cn2nnc3c(N4CC[C@H](O)C4)nc(C(C)(C)C)nc32)N=N1]

In analogy to the procedure described for the synthesis of 4-{[5-tert-butyl-7-(3,3-difluoropyrrolidin-1-yl)-3H-[1,2,3]triazolo[4,5-d]pyrimidin-3-yl]methyl}-N-{2-[3-(but-3-yn-1-yl)-3H-diaziren-3-yl]ethyl}-1,2,5-oxadiazole-3-carboxamide (example 9, step c) the title compound was prepared from (3S)-1-(5-tert-butyl-3H-triazolo[4,5-d]pyrimidin-7-yl)pyrrolidin-3-ol (CAS 1433946-74-7, 31 mg, 0.12 mmol, 1.0 equiv), (4-((2-(3-(but-3-yn-1-yl)-3H-diazirin-3-yl)ethyl)carbamoyl)-1,2,5-oxadiazol-3-yl)methyl methanesulfonate (40 mg, 0.12 mmol, 1.0 equiv) and NEt$_3$ (33 µL, 0.23 mmol, 2.0 equiv) and isolated as colorless oil (8 mg, 0.016 mmol, 13% yield). HRMS (ESI+) 508.2525 (M+H$^+$).

Example 11

5-[Difluoro(phenyl)methyl]-3-[(2-ethynylphenyl)methyl]-7-(1,2,6-triazaspiro[2.4]hept-1-en-6-yl)triazolo[4,5-d]pyrimidine

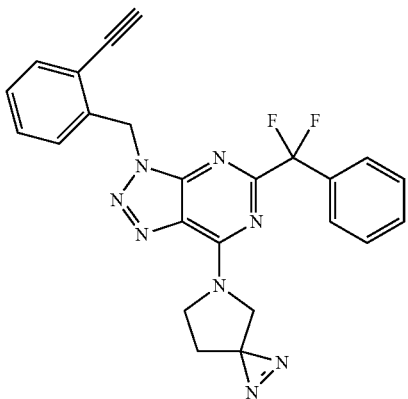 [SMILES: C#Cc1ccccc1Cn1nnc2c(N3CCC4(C3)N=N4)nc(C(F)(F)c3ccccc3)nc21]

a) 5-Amino-1-(2-ethynylbenzyl)-1H-1,2,3-triazole-4-carboxamide

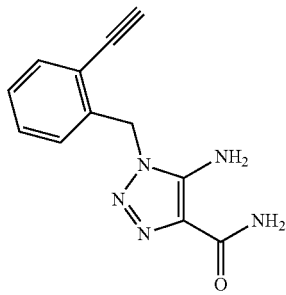 [SMILES: C#Cc1ccccc1Cn1nnc(C(N)=O)c1N]

In analogy for the procedure described for the synthesis of 5-amino-1-(2-chlorobenzyl)-1H-1,2,3-triazole-4-carboxamide (CAS 93444-91-8) in US Patent 2013/116236 A1), the compound was synthesized from 2-ethynylbenzyl methanesulfonate (2.20 g, 10.5 mmol, 1.00 equiv), 2-cyanoacetamide (1.32 g, 15.7 mmol, 1.5 equiv) and sodium azide (714 mg, 11.0 mmol, 1.05 equiv), and isolated as beige solid (1.81 g, 7.50 mmol, 72%). HRMS (ESI+) 264.0855 (M+Na$^+$).

b) 7-Chloro-5-(difluoro(phenyl)methyl)-3-(2-ethynylbenzyl)-3H-[1,2,3]triazolo[4,5-d]pyrimidine

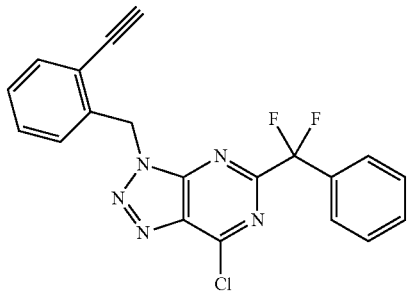 [SMILES: C#Cc1ccccc1Cn1nnc2c(Cl)nc(C(F)(F)c3ccccc3)nc21]

5-Amino-1-(2-ethynylbenzyl)-1H-1,2,3-triazole-4-carboxamide (482 mg, 2.00 mmol, 1.00 equiv), 2,2-difluoro-2-phenylacetonitrile (CAS 2002-72-4, 487 mg, 3.18 mol, 1.59 equiv) and potassium carbonate (1.38 g, 10.0 mmol, 5.00 equiv) was combined with DMF (6.7 mL). The flask was sealed and heated at 90° C. for 3 h. After cooling to rt, 1 M aq. HCl (25 mL) was added. The precipitate was isolated by filtration and dried (azeotropic distillation with toluene) to yield crude material. The crude was dissolved in a mixture of CH$_2$Cl$_2$ (5 mL) and toluene (5 mL). DMF (3 drops) and oxalyl chloride (350 µL, 4.00 mmol, 2.00 equiv) were added and the reaction mixture was heated to 65° C. Upon full conversion as judged by TLC analysis, the mixture was diluted with EtOAc (100 mL) and washed with sat. sodium bicarbonate, 5% aq. LiCl and brine. Drying over MgSO$_4$, filtration and concentration followed by flash chromatography on silica (5% EtOAc in hexanes) afforded the title compound (450 mg, 1.14 mmol, 57%).

c) 5-[Difluoro(phenyl)methyl]-3-[(2-ethynylphenyl)methyl]-7-(1,2,6-triazaspiro[2.4]hept-1-en-6-yl)triazolo[4,5-d]pyrimidine In analogy to the procedure described for the synthesis of 5-tert-Butyl-3-[(2-ethynylphenyl)methyl]-7-(1,2,5-triazaspiro[2.4]hept-1-en-5-yl)-3H-[1,2,3]triazolo[4,5-d]pyrimidine (example 5, step d) the title compound was prepared from 7-chloro-5-(difluoro(phenyl)methyl)-3-(2-ethynylbenzyl)-3H-[1,2,3]triazolo[4,5-d]pyrimidine (50 mg, 0.13 mmol), NEt₃ (26 µL, 0.25 mmol, 1.5 equiv) and the corresponding amine salt (1.5 equiv) and isolated as colorless foam (45 mg, 0.10 mmol, 78% yield). HRMS (ESI+) 479.1513 (M+Na₊).

Example 12

5-[Difluoro(phenyl)methyl]-7-(3,3-difluoropyrrolidin-1-yl)-3-[[2-ethynyl-6-[3-(trifluoromethyl)diazirin-3-yl]phenyl]methyl]triazolo[4,5-d]pyrimidine

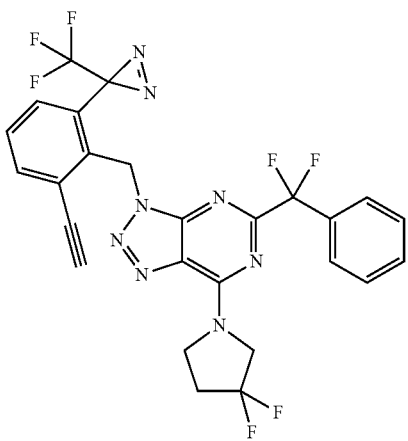 [SMILES: C#Cc1cccc(C2(C(F)(F)F)N=N2)c1Cn1nnc2c(N3CCC(F)(F)C3)nc(C(F)(F)c3ccccc3)nc21]

a) 2,6-Diiodobenzyl alcohol

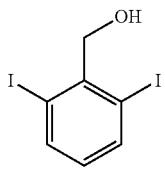

2,6-Diiodibenzoic acid (CAS 194084-84-9, 2.13 g, 5.35 mmol, 1.00 equiv) was suspended in CH₂Cl₂ (10.7 mL). DMF (3 drops) and oxalyl chloride (0.52 mL, 5.9 mmol, 1.1 equiv) were added. When bubbling ceased, the reaction mixture was heated to reflux for 30 minutes (TLC indicated full consumption of starting material). It was diluted with CH₂Cl₂, washed with sat. aq. sodium bicarbonate and brine, dried over MgSO₄, filtered and concentrated. The crude acid chloride was dissolved in a 1:1 mixture of MeCN and THF (30 mL). NaBH₄ (405 mg, 10.7 mmol, 2.00 equiv) was added in portions at rt (exotherm). After 30 min TLC indicated full conversion of acid chloride. MeOH (5 mL) was added slowly and the resulting mixture was diluted with water. Extraction with EtOAc (3×100 mL), washing with brine (100 mL), drying over MgSO₄, filtration and concentration followed by flash chromatography on silica (15% EtOAc in hexanes to 20% to 50%) afforded the title compound as colorless solid (1.55 g, 4.31 mmol, 80%). HRMS (MALDI) 382.8399 (M+Na⁺).

b) 1,3-Diiodo-2-(((4-methoxybenzyl)oxy)methyl)benzene

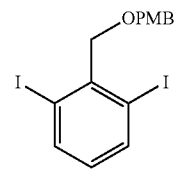

2,6-Diiodobenzyl alcohol (1.61 g, 4.47 mmol, 1.00 equiv) was dissolved in DMF and cooled to 0° C. NaH (60% in mineral oil, 215 mg, 5.37 mmol, 1.20 equiv) was added and the mixture was stirred for 20 min. 4-Methoxybenzyl chloride (0.67 mL, 4.9 mmol, 1.1 equiv) was added and the cooling bath was removed. After 30 min, the reaction was quenched by the addition of sat. aq. NH₄Cl (5 mL). The mix was extracted with EtOAc (3×50 mL). The combined organics were washed with 5% aq. LiCl (50 mL) and brine (50 mL), dried over MgSO₄, filtered and concentrated. Flash chromatography on silica (5% EtOAc in hexanes) afforded the title compound as colorless solid (1.9 g, 4.0 mmol, 88%). HRMS (MALDI) 479.9078 (M+).

c) 2,2,2-Trifluoro-1-(3-iodo-2-(((4-methoxybenzyl)oxy)methyl)phenyl)ethanone

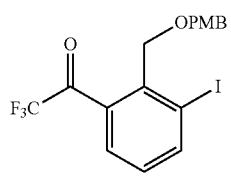

1,3-Diiodo-2-(((4-methoxybenzyl)oxy)methyl)benzene (1.9 g, 4.0 mmol, 1.0 equiv) was dissolved in THF (8 mL) and cooled to −30° C. A solution of iPrMgCl—LiCl (0.87 M, 5.0 mL, 4.35 mmol, 1.10 equiv) was added and the resulting solution was stirred for 2.5 h, while the temperature was allowed to rise to −20° C. N-methoxy-N-methyltrifluoroacetamide (0.68 g, 4.4 mmol, 1.1 equiv) was added, the cooling bath was removed and the reaction was stirred overnight. Sat. aq. NH₄Cl was added and it was extracted with EtOAc. The organics were washed with brine, dried over MgSO₄, filtered and concentrated. Flash chromatography on silica afforded the title compound as colorless oil (1.04 g, 2.31 mmol, 58%). ¹H NMR (400 MHz, CDCl₃) δ 7.95 (dd, J=7.9, 1.2 Hz, 1H), 7.35 (dd, J=7.6, 1.0 Hz, 1H), 7.25 (d, J=8.1 Hz, 2H), 7.09 (t, J=7.8 Hz, 1H), 6.90 (d, J=8.7 Hz, 2H), 4.57 (s, 2H), 4.48 (s, 2H), 3.82 (s, 3H).

c) 2,2,2-Trifluoro-1-(3-iodo-2-(((4-methoxybenzyl)oxy)methyl)phenyl)ethanone oxime

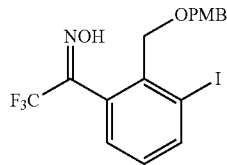

2,2,2-Trifluoro-1-(3-iodo-2-(((4-methoxybenzyl)oxy)methyl)phenyl)ethanone (1.04 g, 2.31 mmol, 1.00 equiv) was combined with EtOH (4.6 mL), hydroxylamine hydrochloride (193 mg, 2.77 mmol, 1.20 equiv) and pyridine (0.28 mL, 3.5 mmol, 1.5 equiv). The mixture was heated at 80° C. until TLC indicated full consumption of starting material. Concentration and flash chromatography on silica afforded the title compound (680 mg, 1.46 mmol, 63%).

d) 2,2,2-Trifluoro-1-(3-iodo-2-(((4-methoxybenzyl)oxy)methyl)phenyl)ethanone O-tosyl oxime

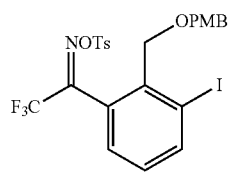

2,2,2-Trifluoro-1-(3-iodo-2-(((4-methoxybenzyl)oxy)methyl)phenyl)ethanone oxime (680 mg, 1.46 mmol, 1.00 equiv) was dissolved in $CH_2Cl_2$ (3 mL). TsCl (307 mg, 1.61 mmol, 1.10 equiv) and DMAP (18 mg, 0.15 mmol, 0.10 equiv) were added and the mixture was stirred at rt. When TLC indicated full consumption of starting material, water was added. Extraction with $CH_2Cl_2$, washing with brine, drying over $MgSO_4$, filtration and concentration followed by flash chromatography afforded the title compound as a 2:1 mixture of diastereomers (529 mg, 0.85 mmol, 58%).

e) 3-(3-Iodo-2-(((4-methoxybenzyl)oxy)methyl)phenyl)-3-(trifluoromethyl)-3H-diazirine

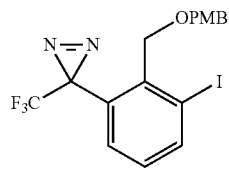

2,2,2-Trifluoro-1-(3-iodo-2-(((4-methoxybenzyl)oxy)methyl)phenyl)ethanone O-tosyl oxime (529 mg, 0.85 mmol, 1.00 equiv) was dissolved in $Et_2O$ (6 mL) and cooled to −78° C. Ammonia (ca. 6 mL) was then introduced and the reaction mix was stirred at reflux for 4 h. The cooling bath was removed and the volatiles were removed. The residue was suspended in diethyl ether and filtered. The filtrate was concentrated. MeOH (10 mL) was added and removed under reduced pressure (2×) to remove residual ammonia. The residue was dissolved in MeOH (10 mL) and combined with $NEt_3$ (0.6 mL, 4.3 mmol, 5.0 equiv). The mixture was titrated with a solution of iodine in MeOH until a yellow-brown color persisted. The mix was diluted with water (200 mL) and sat. aq. sodium thiosulfate (2 mL). Extraction with EtOAc (3×50 mL), washing with brine (50 mL), drying over $MgSO_4$, filtration and concentration followed by flash chromatography on silica afforded the title compound as light-yellow oil (211 mg, 0.46 mmol, 54%). $^1$H NMR (300 MHz, $CDCl_3$) δ 7.97 (dt, J=8.0, 1.0 Hz, 1H), 7.65 (d, J=7.7 Hz, 1H), 7.44-7.37 (m, 2H), 7.06 (td, J=7.8, 0.8 Hz, 1H), 6.93-6.88 (m, 2H), 4.89 (s, 2H), 4.68 (s, 2H), 3.82 (d, J=0.8 Hz, 3H).

f) 3-(2-(((4-Methoxybenzyl)oxy)methyl)-3-((trimethylsilyl)ethynyl)phenyl)-3-(trifluoromethyl)-3H-diazirine

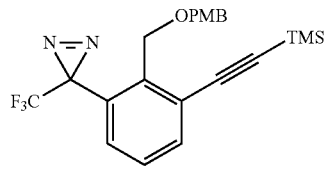

3-(3-odo-2-(((4-methoxybenzyl)oxy)methyl)phenyl)-3-(trifluoromethyl)-3H-diazirine (196 mg, 0.424 mmol, 1.00 equiv) was combined with DMF (1.4 mL, degassed by the freeze-pump-thaw method), $PdCl_2(PPh_3)_2$ (30 mg, 0.042 mmol, 0.10 equiv), CuI (16 mg, 0.085 mmol, 0.20 equiv) and $NEt_3$ (0.12 mL, 0.85 mmol, 2.0 equiv). Trimethylsilylacetylene (89 µL, 0.64 mmol, 1.5 equiv) was added and the mixture was stirred at rt for 20 min. The reaction mixture was diluted with 5% aq. LiCl and extracted with diethyl ether. The organics were washed with 5% aq. LiCl and brine, dried over $MgSO_4$, filtered and concentrated. Flash chromatography on silica (2% EtOAc in hexanes) afforded the title compound as yellow oil (146 mg, 0.34 mmol, 80%). HRMS (ESI+) 450.1819 (M+$NH_4^+$).

g) 3-(3-Ethynyl-2-(((4-methoxybenzyl)oxy)methyl)phenyl)-3-(trifluoromethyl)-3H-diazirine

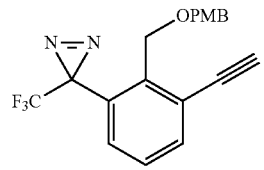

3-(2-(((4-Methoxybenzyl)oxy)methyl)-3-((trimethylsilyl)ethynyl)phenyl)-3-(trifluoromethyl)-3H-diazirine (146 mg, 0.338 mmol, 1.00 equiv) was dissolved in MeOH (1 mL) and $K_2CO_3$ (52 mg, 0.38 mmol, 1.1 equiv) was added. After 1.5 h, sat. aq. $NH_4Cl$ was added the the mixture was extracted with $Et_2O$ (3×30 mL). The organics were washed with brine, dried over $MgSO_4$, filtered and concentrated. Flash chromatography on silica (3% EtOAc in hexanes) afforded the title compound as yellow oil. HRMS (ESI$^+$) 383.0978 (M+Na$^+$).

h) 2-Ethynyl-6-(3-(trifluoromethyl)-3H-diazirin-3-yl)benzyl methanesulfonate

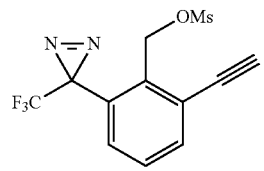 [SMILES: C#Cc1cccc(C2(C(F)(F)F)N=N2)c1COS(C)(=O)=O]

3-(3-Ethynyl-2-(((4-methoxybenzyl)oxy)methyl)phenyl)-3-(trifluoromethyl)-3H-diazirine (318 mg, 0.883 mmol, 1.00 equiv) combined with $CH_2Cl_2$ (8 mL) and $H_2O$ (0.8 mL) at 0° C. DDQ (301 mg, 1.32 mmol, 1.50 equiv) was added and it was stirred until TLC indicated full consumption of starting material. Sat. aq. sodium bicarbonate was added and the mix was extracted with CH$_2$Cl$_2$. The organics were dried over MgSO$_4$, filtered and concentrated. Filtration over a plug of silica (20% EtOAc in hexanes) afforded a mixture of intermediate benzyl alcohol and p-anisaldehyde. The mixture was dissolved in CH$_2$Cl$_2$ (8 mL) and cooled to 0° C. NEt$_3$ (0.18 mL, 1.3 mmol, 1.5 equiv) was added followed by MsCl (76 µL, 0.97 mmol, 1.1 equiv). After 20 min, the reaction was quenched by the addition of sat. aq. sodium bicarbonate, extracted with CH$_2$Cl$_2$, dried over MgSO$_4$, filtered and concentrated. Flash chromatography on silica (15% EtOAc in hexanes) afforded the title compound as colorless oil (244 mg, 0.767 mmol, 87%). The material turned red upon standing and solidified in the freezer. HRMS (ESI$^+$) 341.0178 (M+Na$^+$).

i) 5-(Difluoro(phenyl)methyl)-3-(4-methoxybenzyl)-3H-[1,2,3]triazolo[4,5-d]pyrimidin-7(4H)-one

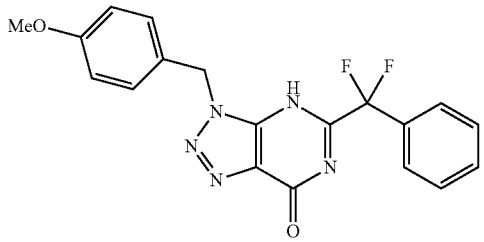 [SMILES: COc1ccc(Cn2nnc3c(=O)nc(C(F)(F)c4ccccc4)[nH]c32)cc1]

In analogy to the procedure described for the synthesis of 5-(difluoro(phenyl)methyl)-3-(2-(trifluoromethyl)benzyl)-3H-[1,2,3]triazolo[4,5-d]pyrimidin-7(4H)-one (example 2, step b) the title compound was prepared from 5-amino-1-(4-methoxybenzyl)-1H-1,2,3-triazole-4-carboxamide (CAS 133992-53-7, 2.0 g, 8.1 mmol, 1.0 equiv) and 2,2-difluoro-2-phenylacetonitrile and isolated as colorless solid (2.0 g, 5.2 mmol, 65%). $^1$H NMR (400 MHz, DMSO) δ 13.57 (s, 1H), 7.75-7.66 (m, 2H), 7.64-7.53 (m, 3H), 7.27 (d, J=8.4 Hz, 2H), 6.88 (d, J=8.2 Hz, 2H), 5.64 (s, 2H), 3.72 (s, 3H).

j) 7-Chloro-5-(difluoro(phenyl)methyl)-3-(4-methoxybenzyl)-3H-[1,2,3]triazolo[4,5-d]pyrimidine

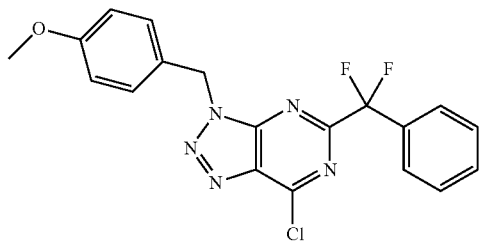 [SMILES: COc1ccc(Cn2nnc3c(Cl)nc(C(F)(F)c4ccccc4)nc32)cc1]

In analogy to the procedure described for the synthesis of 3-((5-(tert-Butyl)-7-chloro-3H-[1,2,3]triazolo[4,5-d]pyrimidin-3-yl)methyl)-4-methyl-1,2,5-oxadiazole (example 1, step a) the title compound was prepared from 5-(Difluoro(phenyl)methyl)-3-(4-methoxybenzyl)-3H-[1,2,3]triazolo[4,5-d]pyrimidin-7(4H)-one and isolated as colorless solid (1.21 g, 3.01 mmol, 93%). HRMS (ESI$^+$) 402.0928 (M+H$^+$).

k) 5-(Difluoro(phenyl)methyl)-7-(3,3-difluoropyrrolidin-1-yl)-3-(4-methoxybenzyl)-3H-[1,2,3]triazolo[4,5-d]pyrimidine

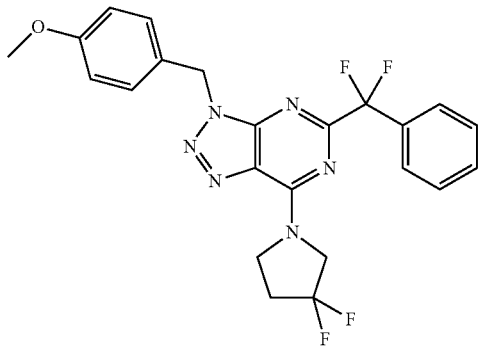 [SMILES: COc1ccc(Cn2nnc3c(N4CCC(F)(F)C4)nc(C(F)(F)c4ccccc4)nc32)cc1]

In analogy to the procedure described for the synthesis of 5-tert-butyl-3-[(4-methyl-1,2,5-oxadiazol-3-yl)methyl]-7-(1,2,5-triazaspiro[2.4]hept-1-en-5-yl)-3H-[1,2,3]triazolo[4,5-d]pyrimidine (example 1, step d) the title compound was prepared from 7-chloro-5-(difluoro(phenyl)methyl)-3-(4-methoxybenzyl)-3H-[1,2,3]triazolo[4,5-d]pyrimidine (622 mg, 1.55 mmol, 1.00 equiv) and 3,3-difluoropyrrolidine hydrochloride (244 mg, 1.70 mmol, 1.10 equiv) and isolated as colorless solid (600 mg, 1.27 mmol, 82%). HRMS (ESI$^+$) 473.1707 (M+H$^+$).

l) 5-(Difluoro(phenyl)methyl)-7-(3,3-difluoropyrrolidin-1-yl)-3H-[1,2,3]triazolo[4,5-d]pyrimidine

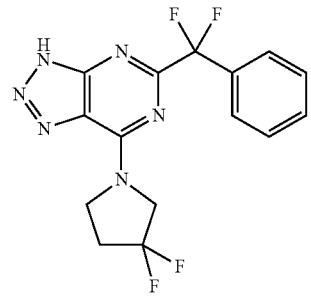 [SMILES: FC1(F)CCN(c2nc(C(F)(F)c3ccccc3)nc3[nH]nnc23)C1]

5-(Difluoro(phenyl)methyl)-7-(3,3-difluoropyrrolidin-1-yl)-3-(4-methoxybenzyl)-3H-[1,2,3]triazolo[4,5-d]pyrimidine (200 mg. 0.423 mmol. 1.00 equiv) was combined with anisole (1.40 mL, 12.8 mmol, 30.3 equiv) and trifluoroacetic acid (6.5 mL) and heated at 65° C. for 5 h. After removal of the volatiles, the residue was taken up in EtOAc (50 mL) and washed with aq. NaOH (1 M, 3×10 mL). The aqueous phase was backextracted with EtOAc (2×20 mL). The combined organics were washed with brine, dried over MgSO$_4$, filtered and concentrated. Flash chromatography on silica (50% EtOAc in hexanes to 100%) afforded product contaminated with an unidentified byproduct. The solid was triturated with EtOH and filtered to leave a tan solid. The washings were concentrated and the residue was triturated with 20% EtOAc in hexanes. The suspension was filtered and the filtercake washed with the same solvent mixture to give another crop of the product (74 mg in total, 0.21 mmol, 50%). HRMS (ESI$^+$) 353.1136 (M+H$^+$).

m) 5-[Difluoro(phenyl)methyl]-7-(3,3-difluoropyrrolidin-1-yl)-3-[[2-ethynyl-6-[3-(trifluoromethyl)diazirin-3-yl]phenyl]methyl]triazolo[4,5-d]pyrimidine
In analogy to the procedure described for the synthesis of 5-tert-butyl-7-(3,3-difluoropyrrolidin-1-yl)-3-({2-[3-(trifluoromethyl)-3H-diaziren-3-yl]phenyl}methyl)-3H-[1,2,3]triazolo[4,5-d]pyrimidine (example 4, step d) the title compound was prepared from 5-(difluoro(phenyl)methyl)-7-(3,3-difluoropyrrolidin-1-yl)-3H-[1,2,3]triazolo[4,5-d]pyrimidine (23 mg, 0.065 mmol, 1.00 equiv) and 2-ethynyl-6-(3-(trifluoromethyl)-3H-diazirin-3-yl)benzyl methanesulfonate (27 mg, 0.085 mmol, 1.3 equiv) and isolated as light-yellow oil (11 mg, 0.019 mmol, 29% yield). HRMS (ESI+) 575.1537 (M+H$^+$).

Example 13

5-tert-Butyl-7-(3,3-difluoropyrrolidin-1-yl)-3-[[2-ethynyl-6-[3-(trifluoromethyl)diazirin-3-yl]phenyl]methyl]triazolo[4,5-d]pyrimidine

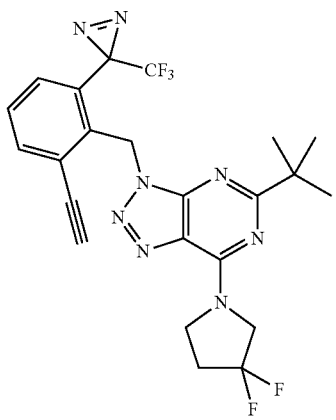 [SMILES: C#Cc1cccc(C2(C(F)(F)F)N=N2)c1Cn1nnc2c(N3CCC(F)(F)C3)nc(C(C)(C)C)nc21]

5-tert-Butyl-7-(3,3-difluoropyrrolidin-1-yl)-3H-[1,2,3]triazolo[4,5-d]pyrimidine (CAS 1438465-59-8, 23 mg, 0.072 mmol, 1.0 equiv) and 2-ethynyl-6-(3-(trifluoromethyl)-3H-diazirin-3-yl)benzyl methanesulfonate (24 mg, 0.085 mmol, 1.2 equiv) were dissolved in DMF (0.5 mL). Trimethylamine (20 µL, 0.15 mmol, 2.0 equiv) was added and it was stirred overnight at room temperature. The reaction mixture was diluted with EtOAc (60 mL), washed with 5% aq. LiCl (2×20 mL) and brine (1×20 mL), dried over MgSO$_4$, filtered and concentrated. Flash chromatography on silica (5% EtOAc in hexanes) afforded the title compound as colorless oil (14 mg, 0.028 mmol, 38%). HRMS (ESI$^+$) 505.1881 (M+H$^+$).

Example 14

(3S)-1-[5-tert-Butyl-3-[[2-ethynyl-6-[3-(trifluoromethyl)diazirin-3-yl]phenyl]methyl]triazolo[4,5-d]pyrimidin-7-yl]pyrrolidin-3-ol

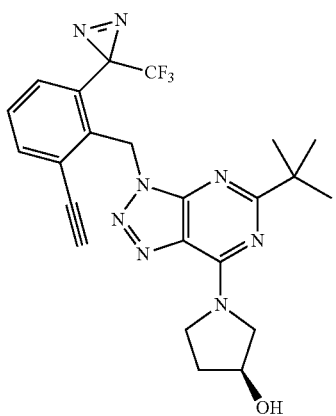 [SMILES: C#Cc1cccc(C2(C(F)(F)F)N=N2)c1Cn1nnc2c(N3CC[C@H](O)C3)nc(C(C)(C)C)nc21]

(3S)-1-(5-tert-butyl-3H-triazolo[4,5-d]pyrimidin-7-yl)pyrrolidin-3-ol (23 mg, 0.088 mmol, 1.20 equiv) and 2-ethynyl-6-(3-(trifluoromethyl)-3H-diazirin-3-yl)benzyl methanesulfonate (23 mg, 0.072 mmol, 1.00 equiv) were dissolved in DMF (0.5 mL). Triethylamine (15 µL, 0.11 mmol, 1.5 equiv) was added and it was stirred overnight. The reaction mixture was diluted with EtOAc (60 mL), washed with 5% aq. LiCl (2×20 mL) and brine (1×20 mL), dried over MgSO$_4$, filtered and concentrated. The crude was purified by flash chromatography on silica (30% EtOAc in hexanes+5% AcOH). Fractions containing product were pooled, washed with sat. NaHCO$_3$ and brine, dried over MgSO$_4$, filtered and concentrated to yield the title compound as colorless oil (8 mg, 0.017 mmol, 23%). HRMS (ESI$^+$) 485.2018 (M+H$^+$).

Example 15

(3S)-1-[5-[Difluoro(phenyl)methyl]-3-[[2-ethynyl-6-[3-(trifluoromethyl)diazirin-3-yl]phenyl]methyl]triazolo[4,5-d]pyrimidin-7-yl]pyrrolidin-3-ol

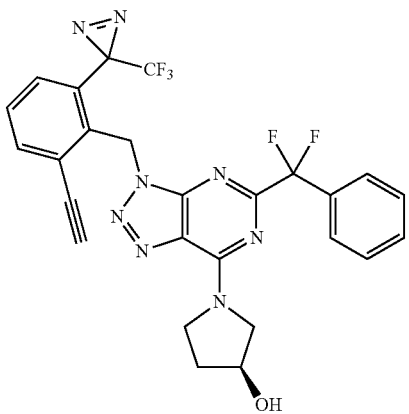 [SMILES: C#Cc1cccc(C2(C(F)(F)F)N=N2)c1Cn1nnc2c(N3CC[C@H](O)C3)nc(C(F)(F)c3ccccc3)nc21]

a) (S)-1-(5-(Difluoro(phenyl)methyl)-3-(4-methoxybenzyl)-3H-[1,2,3]triazolo[4,5-d]pyrimidin-7-yl)pyrrolidin-3-ol

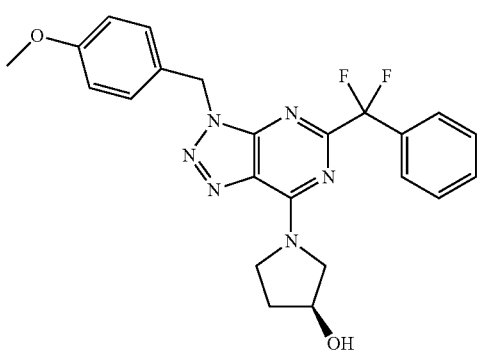 [SMILES: COc1ccc(Cn2nnc3c(N4CC[C@H](O)C4)nc(C(F)(F)c4ccccc4)nc32)cc1]

In analogy to the procedure described for the synthesis of 5-tert-butyl-3-[(4-methyl-1,2,5-oxadiazol-3-yl)methyl]-7-(1,2,5-triazaspiro[2.4]hept-1-en-5-yl)-3H-[1,2,3]triazolo[4,5-d]pyrimidine (example 1, step d) the title compound was prepared from 7-chloro-5-(difluoro(phenyl)methyl)-3-(4-methoxybenzyl)-3H-[1,2,3]triazolo[4,5-d]pyrimidine (272 mg, 0.677 mmol, 1.00 equiv) and (S)-pyrrolidin-3-ol (65 mg, 0.75 mmol, 1.1 equiv) and isolated as colorless foam (291 mg, 0.643 mmol, 95%). HRMS (ESI$^+$) 453.1850 (M+H$^+$).

b) (S)-1-(5-(Difluoro(phenyl)methyl)-3H-[1,2,3]triazolo[4,5-d]pyrimidin-7-yl)pyrrolidin-3-ol

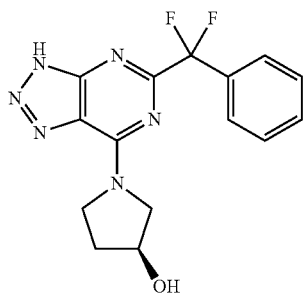 [SMILES: O[C@H]1CCN(c2nc(C(F)(F)c3ccccc3)nc3[nH]nnc23)C1]

(S)-1-(5-(Difluoro(phenyl)methyl)-3-(4-methoxybenzyl)-3H-[1,2,3]triazolo[4,5-d]pyrimidin-7-yl)pyrrolidin-3-ol (141 mg, 0.312 mmol) was dissolved in trifluoroacetic acid (4.38 mL) and heated to 70° C. for 3 h. LCMS indicated the formation of product and of the respective trifluoroacetyl ester. After removal of the volatiles the residue was dissolved in MeOH (3 mL) and THF (3 mL). $K_2CO_3$ (215 mg, 1.59 mmol, 5.0 equiv) was added and it stirred for 30 minutes. LCMS indicates mainly desired product and a small amount of both isomers of the starting material, presumably due to non-selective reaction of the desired product with benzyltrifluoroacetate as alkylating agent. The reaction mix was neutralized with dilute HCl and concentrated. Flash chromatography on silica (5% MeOH in EtOAc to 10% to 30%) yielded a colorless solid (220 mg). The material was partitioned between EtOAc and sat. $NaHCO_3$. The aq. phase was removed. The organic phase was washed with brine, dried over $MgSO_4$, filtered and concentrated to give the title compound as yellowish solid (69 mg, 0.21 mmol, 67%).

c) (3S)-1-[5-[Difluoro(phenyl)methyl]-3-[[2-ethynyl-6-[3-(trifluoromethyl)diazirin-3-yl]phenyl]methyl]triazolo[4,5-d]pyrimidin-7-yl]pyrrolidin-3-ol (S)-1-(5-(Difluoro(phenyl)methyl)-3H-[1,2,3]triazolo[4,5-d]pyrimidin-7-yl)pyrrolidin-3-ol (32 mg, 0.096 mmol, 1.0 equiv) and 2-ethynyl-6-(3-(trifluoromethyl)-3H-diazirin-3-yl)benzyl methanesulfonate (31 mg, 0.097 mmol, 1.0 equiv) were dissolved in DMF (0.5 mL). DIPEA (25 µL, 0.15 mmol, 1.5 equiv) was added and the mixture was stirred overnight at room temperature. The reaction mixture was diluted with EtOAc (50 mL), washed with 5% aq. LiCl (2×20 mL) and brine (1×20 mL), dried over $MgSO_4$, filtered and concentrated. Preparative TLC (20% EtOAc in hexanes+20% AcOH) afforded the title compound as colorless wax (18 mg, 0.032 mmol, 34%). HRMS (ESI$^+$) 555.1676 (M+H$^+$).

Example 16

Pharmacological Tests

The following tests were carried out in order to determine the activity of the compounds of formula (I):

Radioligand Binding Assay

The affinity of the compounds of the invention for cannabinoid receptors was determined using recommended amounts of membrane preparations (PerkinElmer) of human embryonic kidney (HEK) cells expressing the human CNR1 or CNR2 receptors in conjunction with 1.5 or 2.6 nM [3H]-CP-55,940 (Perkin Elmer) as radioligand, respectively. Binding was performed in binding buffer (50 mM Tris, 5 mM $MgCl_2$, 2.5 mM EDTA, and 0.5% (wt/vol) fatty acid free BSA, pH 7.4 for CB1 receptor and 50 mM Tris, 5 mM $MgCl_2$, 2.5 mM EGTA, and 0.1% (wt/vol) fatty acid free BSA, pH 7.4 for CB2 receptor) in a total volume of 0.2 mL for 1 h at 30° C. shaking. The reaction was terminated by rapid filtration through microfiltration plates coated with 0.5% polyethylenimine (UniFilter GF/B filter plate; Packard). Bound radioactivity was analyzed for Ki using non-linear regression analysis (Activity Base, ID Business Solution, Limited), with the Kd values for [$^3$H]CP55,940 determined from saturation experiments. The compounds of formula (I) show an excellent affinity for the CB2 receptor with affinities below 10 µM, more particularly of 1 nM to 3 µM and most particularly of 1 nM to 100 nM.

The compounds according to formula (I) have an activity in the above assay (Ki) particularly of 0.5 nM to 10 µM, more particularly of 0.5 nM to 3 µM and most particularly of 0.5 nM to 100 nM.

All compounds are CB2 binders with Ki values below 3 uM and selectivity versus CB1 in the corresponding assay of at least 9 fold.

| Example | human CB2 Ki [µM] | human CB1 Ki [µM] |
|---|---|---|
| 1 | 0.0161 | 2.963 |
| 2 | 0.0008 | 0.993 |
| 3 | 0.0033 | 0.321 |
| 4 | 0.0042 | 0.488 |
| 5 | 0.0056 | 0.132 |
| 6 | 0.0099 | 0.799 |
| 7 | 0.0455 | 5.411 |
| 8 | 0.0556 | >10.000 |
| 9 | 1.1609 | >10.000 |
| 10 | 0.1999 | >10.000 |
| 11 | 0.019 | 0.465 |
| 12 | 0.031 | 3.393 |
| 13 | 0.009 | 0.147 |
| 14 | 0.012 | >10.000 |
| 15 | 0.058 | >10.000 | cAMP Assay

CHO cells expressing human CB1 or CB2 receptors are seeded 17-24 hours prior to the experiment 50.000 cells per well in a black 96 well plate with flat clear bottom (Corning Costar #3904) in DMEM (Invitrogen No. 31331), 1×HT supplement, with 10% fetal calf serum and incubated at 5% $CO_2$ and 37° C. in a humidified incubator. The growth medium was exchanged with Krebs Ringer Bicarbonate buffer with 1 mM IBMX and incubated at 30° C. for 30 min. Compounds were added to a final assay volume of 100 µL and incubated for 30 min at 30° C. Using the cAMP-Nano-TRF detection kit the assay (Roche Diagnostics) was stopped by the addition of 50 µL lysis reagent (Tris, NaCl, 1.5% Triton X100, 2.5% NP40, 10% $NaN_3$) and 50 µL detection solutions (20 µM mAb Alexa700-cAMP 1:1, and 48 µM Ruthenium-2-AHA-cAMP) and shaken for 2 h at room temperature. The time-resolved energy transfer is measured by a TRF reader (Evotec Technologies GmbH), equipped with a ND:YAG laser as excitation source. The plate is measured twice with the excitation at 355 nm and at the emission with a delay of 100 ns and a gate of 100 ns, total exposure time 10 s at 730 (bandwidth 30 nm) or 645 nm (bandwidth 75 nm), respectively. The FRET signal is calculated as follows: FRET=T730-Alexa730-P(T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 µM to 0.13 nM cAMP.

$EC_{50}$ values were determined using Activity Base analysis (ID Business Solution, Limited). The $EC_{50}$ values for a wide range of cannabinoid agonists generated from this assay were in agreement with the values published in the scientific literature.

β-Arrestin translocation assay-PathHunter™ (DiscoveRx)

PathHunter™ β-arrestin CHO-K1 CNR1 cell line (catalog number #93-0200C2) and the β-arrestin CHO-K1 CNR2 cell line (catalog number #93-0706C2) were purchased from DiscoveRx Corporation. The cell line was engineered to express the β-galactosidase EA fragment fused to β-arrestin and the ProLink complementary peptide fused to the target receptor. The PathHunter™ protein complementation assay (DiscoveRx Corporation #93-0001) was performed according to the manufacturer's protocol. Assay plates were seeded containing 7500 (CNR1) and 10000 (CNR2) cells in 384 well plates (Corning Costar #3707, white, clear bottom) in 20 µL cell plating reagent 2 (Discoverx #93-0563R2A). After incubation at 37° C. (5% C02, 95% relative humidity) overnight, 5 µL of test compound was added (1% final DMSO concentration) and the incubation continued at 30° C. for 90 min. Detection reagent (12 µL) was then added and the incubation continued at room temperature for 60 min. Plates were then analyzed for a chemiluminescent signal using a Victor $^3$V reader (Perkin Elmer).

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
| --- | --- |
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:
1. A compound of formula (I)

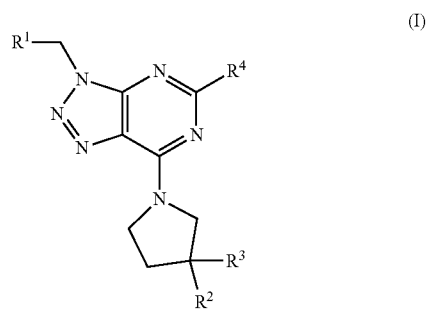

wherein
$R^1$ is a ring selected from phenyl, [1,2,5]oxadiazolyl, pyridinyl, pyrimidinyl and isoxazolyl, wherein said ring is substituted with one or two substituents independently selected from alkyl, haloalkyl, halogen, alkenyl, haloalkyldiazirenyl, alkynyldiazirenylalkylaminocarbonyl, alkynyldiazirenylalkylaminoalkyl, alkynyldiazirenylalkyloxyalkyl, alkynyldiazirenylalkylamino, alkynyldiazirenylalkyloxy and cyano;
$R^2$ and $R^3$ are independently selected from hydrogen, halogen and hydroxyl;
or $R^2$ and $R^3$ together with the carbon atom to which they are attached form diazirenyl;
provided that at least one of $R^1$ or $R^2$ and $R^3$ is a group comprising diazirenyl; and
$R^4$ is alkyl or phenylhaloalkyl;
or a pharmaceutically acceptable salt or ester thereof.
2. The compound according to claim 1, wherein $R^1$ is a ring selected from phenyl or [1,2,5]oxadiazolyl, wherein said ring is substituted with one or two substituents independently selected from alkyl, haloalkyl, haloalkyldiazirenyl, alkynyl, alkynyldiazirenylalkylaminocarbonyl and cyano.

3. The compound according to claim 1, wherein $R^1$ is methyl[1,2,5]oxadiazolyl, trifluoromethylphenyl, trifluoromethyldiazirenylphenyl, ethynylphenyl, butynyldiazirenylethylaminocarbonyl[1,2,5]oxadiazolyl or (trifluoromethyldiazirenyl)(cyano)phenyl.

4. The compound according to claim 1, wherein $R^2$ is hydrogen and $R^3$ is hydroxyl; or $R^2$ and $R^3$ together with the carbon atom to which they are attached form diazirenyl; or $R^2$ and $R^3$ are both fluorine.

5. The compound according to claim 1, wherein $R^4$ is tent-butyl or phenyldifluoromethyl.

6. The compound according to claim 1 selected from the group consisting of:
- 5-tert-butyl-3-[(4-methyl-1,2,5-oxadiazol-3-yl)methyl]-7-(1,2,5-triazaspiro[2.4]hept-1-en-5-yl)-3H-[1,2,3]triazolo[4,5-d]pyrimidine;
- 5-[difluoro(phenyl)methyl]-7-(1,2,5-triazaspiro[2.4]hept-1-en-5-yl)-3-{[2-(trifluoromethyl)phenyl]methyl}-3H-[1,2,3]triazolo[4,5-d]pyrimidine;
- 5-tert-butyl-3-[(2-chlorophenyl)methyl]-7-(1,2,5-triazaspiro[2.4]hept-1-en-5-yl)-3H-[1,2,3]triazolo[4,5-d]pyrimidine;
- 5-tert-butyl-7-(3,3-difluoropyrrolidin-1-yl)-3-({2-[3-(trifluoromethyl)-3H-diaziren-3-yl]phenyl}methyl)-3H-[1,2,3]triazolo[4,5-d]pyrimidine;
- 5-tert-butyl-3-[(2-ethynylphenyl)methyl]-7-(1,2,5-triazaspiro[2.4]hept-1-en-5-yl)-3H-[1,2,3]triazolo[4,5-d]pyrimidine;
- 3-[(2-chlorophenyl)methyl]-5-[difluoro(phenyl)methyl]-7-(1,2,5-triazaspiro[2.4]hept-1-en-5-yl)-3H-[1,2,3]triazolo[4,5-d]pyrimidine;
- 5-[difluoro(phenyl)methyl]-3-[(4-methyl-1,2,5-oxadiazol-3-yl)methyl]-7-(1,2,5-triazaspiro[2.4]hept-1-en-5-yl)-3H-[1,2,3]triazolo[4,5-d]pyrimidine;
- 5-tert-butyl-3-({2-chloro-4-[3-(trifluoromethyl)-3H-diaziren-3-yl]phenyl}methyl)-7-(3,3-difluoropyrrolidin-1-yl)-3H-[1,2,3]triazolo[4,5-d]pyrimidine;
- 4-{[5-tert-butyl-7-(3,3-difluoropyrrolidin-1-yl)-3H-[1,2,3]triazolo[4,5-d]pyrimidin-3-yl]methyl}-N-{2-[3-(but-3-yn-1-yl)-3H-diaziren-3-yl]ethyl}-1,2,5-oxadiazole-3-carboxamide;
- 4-({5-tert-butyl-7-[(3S)-3-hydroxypyrrolidin-1-yl]-3H-[1,2,3]triazolo[4,5-d]pyrimidin-3-yl}methyl)-N-{2-[3-(but-3-yn-1-yl)-3H-diaziren-3-yl]ethyl}-1,2,5-oxadiazole-3-carboxamide;
- N-{2-[3-(but-3-yn-1-yl)-3H-diaziren-3-yl]ethyl}-4-({5-[difluoro(phenyl)methyl]-7-(3,3-difluoropyrrolidin-1-yl)-3H-[1,2,3]triazolo[4,5-d]pyrimidin-3-yl}methyl)-1,2,5-oxadiazole-3-carboxamide;
- 5-tert-butyl-7-(3,3-difluoropyrrolidin-1-yl)-3-({3-[3-(trifluoromethyl)-3H-diaziren-3-yl]pyridin-2-yl}methyl)-3H-[1,2,3]triazolo[4,5-d]pyrimidine;
- 5-[difluoro(phenyl)methyl]-7-(3,3-difluoropyrrolidin-1-yl)-3-({3-[3-(trifluoromethyl)-3H-diaziren-3-yl]pyridin-2-yl}methyl)-3H-[1,2,3]triazolo[4,5-d]pyrimidine;
- (3S)-1-[5-tert-butyl-3-({3-[3-(trifluoromethyl)-3H-diaziren-3-yl]pyridin-2-yl}methyl)-3H-[1,2,3]triazolo[4,5-d]pyrimidin-7-yl]pyrrolidin-3-ol;
- (3S)-1-{5-[difluoro(phenyl)methyl]-3-({3-[3-(trifluoromethyl)-3H-diaziren-3-yl]pyridin-2-yl}methyl)-3H-[1,2,3]triazolo[4,5-d]pyrimidin-7-yl}pyrrolidin-3-ol;
- 5-tert-butyl-7-(3,3-difluoropyrrolidin-1-yl)-3-({4-[3-(trifluoromethyl)-3H-diaziren-3-yl]pyridin-3-yl}methyl)-3H-[1,2,3]triazolo[4,5-d]pyrimidine;
- (3S)-1-[5tert-butyl-3-({4-[3(trifluoromethyl)-3H-diaziren-3-yl]pyridin-3-yl}methyl)-3H-[1,2,3]triazolo[4,5-d]pyrimidin-7-yl]pyrrolidin-3-ol;
- 5-[difluoro(phenyl)methyl]-7-(3,3-difluoropyrrolidin-1-yl)-3-({4-[3-(trifluoromethyl)-3H-diaziren-3-yl]pyridin-3-yl}methyl)-3H-[1,2,3]triazolo[4,5-d]pyrimidine;
- (3S)-1-{5-[difluoro(phenyl)methyl]-3-({4-[3-(trifluoromethyl)-3H-diaziren-3-yl]pyridin-3-yl}methyl)-3H-[1,2,3]triazolo[4,5-d]pyrimidin-7-yl}pyrrolidin-3-ol;
- 5-tert-butyl-7-(3,3-difluoropyrrolidin-1-yl)-3-({5-[3-(trifluoromethyl)-3H-diaziren-3-yl]pyrimidin-4-yl}methyl)-3H-[1,2,3]triazolo[4,5-d]pyrimidine;
- (3S)-1-[5-tert-butyl-3-({5-[3-(trifluoromethyl)-3H-diaziren-3-yl]pyrimidin-4-yl}methyl)-3H-[1,2,3]triazolo[4,5-d]pyrimidin-7-yl]pyrrolidin-3-ol;
- 5-[difluoro(phenyl)methyl]-7-(3,3-difluoropyrrolidin-1-yl)-3-({5-[3-(trifluoromethyl)-3H-diaziren-3-yl]pyrimidin-4-yl}methyl)-3H-[1,2,3]triazolo[4,5-d]pyrimidine;
- (3S)-1-{5-[difluoro(phenyl)methyl]-3-({5-[3-(trifluoromethyl)-3H-diaziren-3-yl]pyrimidin-4-yl}methyl)-3H-[1,2,3]triazolo[4,5-d]pyrimidin-7-yl}pyrrolidin-3-ol;
- 5-tert-butyl-7-(3,3-difluoropyrrolidin-1-yl)-3-({3-[3-(trifluoromethyl)-3H-diaziren-3-yl]pyridin-4-yl}methyl)-3H-[1,2,3]triazolo[4,5-d]pyrimidine;
- (3S)-1-[5-tert-butyl-3-({3-[3(trifluoromethyl)-3H-diaziren-3-yl]pyridin-4-yl}methyl)-3H-[1,2,3]triazolo[4,5-d]pyrimidin-7-yl]pyrrolidin-3-ol;
- 5-[difluoro(phenyl)methyl]-7-(3,3-difluoropyrrolidin-1-yl)-3-({3-[3-(trifluoromethyl)-3H-diaziren-3-yl]pyridin-4-yl}methyl)-3H-[1,2,3]triazolo[4,5-d]pyrimidine;
- (3S)-1-{5-[difluoro(phenyl)methyl]-3-({3-[3-(trifluoromethyl)-3H-diaziren-3-yl]pyridin-4-yl}methyl)-3H-[1,2,3]triazolo[4,5-d]pyrimidin-7-yl}pyrrolidin-3-ol;
- 5-tert-butyl-7-(3,3-difluoropyrrolidin-1-yl)-3-({5-[3-(trifluoromethyl)-3H-diaziren-3-yl]pyridin-2-yl}methyl)-3H-[1,2,3]triazolo[4,5-d]pyrimidine;
- 5-tert-butyl-7-(3,3-difluoropyrrolidin-1-yl)-3-({4-[3-(trifluoromethyl)-3H-diaziren-3-yl]pyridin-2-yl}methyl)-3H-[1,2,3]triazolo[4,5-d]pyrimidine;
- 5-tert-butyl-7-(3,3-difluoropyrrolidin-1-yl)-3-({5-[3-(trifluoromethyl)-3H-diaziren-3-yl]pyridin-3-yl}methyl)-3H-[1,2,3]triazolo[4,5-d]pyrimidine;
- 5-{[5-tert-butyl-7-(3,3-difluoropyrrolidin-1-yl)-3H-[1,2,3]triazolo[4,5-d]pyrimidin-3-yl]methyl}-N-{2-[3-(but-3-yn-1-yl)-3H-diaziren-3-yl]ethyl}-3-methyl-1,2-oxazole-4-carboxamide;
- N-[(4-{[5-tert-butyl-7-(3,3-difluoropyrrolidin-1-yl)-3H-[1,2,3]triazolo[4,5-d]pyrimidin-3-yl]methyl}-1,2,5-oxadiazol-3-yl)methyl]-2-[3-(but-3-yn-1-yl)-3H-diaziren-3-yl]ethan-1-amine;
- 5-tert-butyl-3-{[4-({2-[3(but-3-yn-1-yl)-3H-diaziren-3-yl]ethoxy}methyl)-1,2,5-oxadiazol-3 -yl]methyl}-7-(3,3-difluoropyrrolidin-1-yl)-3H-[1,2,3]triazolo[4,5-d]pyrimidine;
- 2-[3-(but-3-yn-1-yl)-3H-diaziren-3-yl]-N-{[4-({5-[difluoro(phenyl)methyl]-7-(3,3-difluoropyrrolidin-1-yl)-3H-[1,2,3]triazolo[4,5-d]pyrimidin-3-yl}methyl)-1,2,5-oxadiazol-3-yl]methyl}ethan-1-amine;
- 3-{[4-({2-[3-(but-3-yn-1-yl)-3H-diaziren-3-yl]ethoxy}methyl)-1,2,5-oxadiazol-3-yl]methyl}-5-[difluoro(phenyl)methyl]-7-(3,3-difluoropyrrolidin-1-yl)-3H-[1,2,3]triazolo[4,5-d]pyrimidine;
- 5-tert-butyl-3-[(2-{2-[3-(but-3-yn-1-yl)-3H-diaziren-3-yl]ethoxy}phenyl)methyl]-7-(3,3-difluoropyrrolidin-1-yl)-3H-[1,2,3]triazolo[4,5-d]pyrimidine;
- 2-{[5-tert-butyl-7-(3,3-difluoropyrrolidin-1-yl)-3H-[1,2,3]triazolo[4,5-d]pyrimidin-3-yl]methyl}-N-{2-[3-(but-3-yn-1-yl)-3H-diaziren-3-yl]ethyl}aniline;

3-[(2-{2-[3-(but-3-yn-1-yl)-3H-diaziren-3-yl]
ethoxy}phenyl)methyl]-5-[difluoro(phenyl)methyl]-7-
(3,3-difluoropyrrolidin-1-yl)-3H-[1,2,3]triazolo[4,5-d]
pyrimidine;
N-{2-[3-(but-3-yn-1-yl)-3H-diaziren-3-yl]ethyl}-2-({5-
[difluoro(phenyl)methyl]-7-(3,3-difluoropyrrolidin-1-
yl)-3H-[1,2,3]triazolo[4,5-d]pyrimidin-3-yl}methyl)
aniline;
5-[difluoro(phenyl)methyl]-3-[(2-ethynylphenyl)
methyl]-7-(1,2,6-triazaspiro[2.4]hept-1-en-6-yl)tri-
azolo[4,5-d]pyrimidine;
5-[difluoro(phenyl)methyl]-7-(3,3-difluoropyrrolidin-1-
yl)-3-[[2-ethynyl-6-[3-(trifluoromethyl)diazirin-3-yl]
phenyl]methyl]triazolo[4,5-d]pyrimidine;
5-tert-butyl-7-(3,3-difluoropyrrolidin-1-yl)-3-[[2-ethy-
nyl-6-[3(trifluoromethyl)diazirin-3-yl]phenyl]methyl]
triazolo[4,5-d]pyrimidine;
(3S)-1-[5-tert-butyl-3[[2-ethynyl-6-[3-(trifluoromethyl)
diazirin-3-yl]phenyl]methyl]triazolo[4,5-d]pyrimidin-
7-yl]pyrrolidin-3-ol; and
(3S)-1-[5-[difluoro(phenyl)methyl]-3-[[2-ethynyl-6-[3-
(trifluoromethyl)diazirin-3-yl]phenyl]methyl]triazolo
[4,5-d]pyrimidin-7-yl]pyrrolidin-3-ol;
or a pharmaceutically acceptable salt thereof.

7. The compound according to claim 1 selected from the group consisting of:
5-tert-butyl-3-[(4-methyl-1,2,5-oxadiazol-3-yl)methyl]-
7-(1,2,5-triazaspiro[2.4]hept-1-en-5-yl)-3H-[1,2,3]tri-
azolo[4,5-d]pyrimidine;
5-[difluoro(phenyl)methyl]-7-(1,2,5-triazaspiro[2.4]hept-
1-en-5-yl)-3-{[2-(trifluoromethyl)phenyl]methyl}-3H-
[1,2,3]triazolo[4,5-d]pyrimidine;
5-tert-butyl-7-(3,3-difluoropyrrolidin-1-yl)-3-({2-[3-(trif-
luoromethyl)-3H-diaziren-3-yl]phenyl}methyl)-3H-[1,
2,3]triazolo[4,5-d]pyrimidine;
5-tert-butyl-3-[(2-ethynylphenyl)methyl]-7-(1,2,5-triaz-
aspiro[2.4]hept-1-en-5-yl)-3H-[1,2,3]triazolo[4,5-d]
pyrimidine;
4-({5-tert-butyl-7-[(3S)-3-hydroxypyrrolidin-1-yl]-3H-
[1,2,3]triazolo[4,5-d]pyrimidin-3-yl}methyl)-N-{2-[3-
(but-3-yn-1-yl)-3H-diaziren-3-yl]ethyl}-1,2,5-oxadi-
azole-3-carboxamide;
5-[difluoro(phenyl)methyl]-7-(3,3-difluoropyrrolidin-1-
yl)-3-[[2-ethynyl-6-[3-(trifluoromethyl)diazirin-3-yl]
phenyl]methyl]triazolo[4,5-d]pyrimidine; and
(3S)-1-[5-tert-butyl-3-[[2-ethynyl-6-[3-(trifluoromethyl)
diazirin-3-yl]phenyl]methyl]triazolo[4,5-d]pyrimidin-
7-yl]pyrrolidin-3-ol;
or a pharmaceutically acceptable salt thereof.

8. A process for the manufacture of a compound according to claim 1 comprising the reaction of a compound of formula (A)

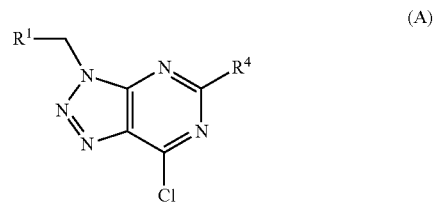

in the presence of a compound of formula (B)

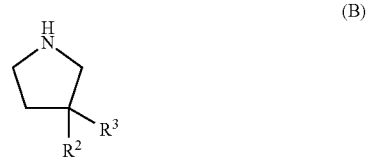

and a base, wherein $R^1$ to $R^4$ are as defined in claim 1.

9. A compound manufactured according to the process of claim 8.

10. A pharmaceutical composition comprising a compound of claim 1, or a pharmaceutically acceptable salt or ester thereof, and a therapeutically inert carrier.

11. A method for the treatment of pain, which method comprises administering an effective amount of a compound of claim 1, or a pharmaceutically acceptable salt or ester thereof, to a patient in need thereof.

12. The compound according to claim 3, wherein $R^2$ is hydrogen and $R^3$ is hydroxyl; or $R^2$ and $R^3$ together with the carbon atom to which they are attached form diazirenyl; or $R^2$ and $R^3$ are both fluorine.

13. The compound according to claim 12, wherein $R^4$ is tent-butyl or phenyldifluoromethyl.

14. The method of claim 11, wherein the pain is a neuropathic pain.

* * * * *